(12) United States Patent
Kita

(10) Patent No.: US 11,668,704 B2
(45) Date of Patent: Jun. 6, 2023

(54) DEGRADATION PREVENTING MEANS FOR IMMUNOASSAY REAGENT CONTAINING INSOLUBLE CARRIER PARTICLES

(71) Applicant: FUJIKURA KASEI CO., LTD., Tokyo (JP)

(72) Inventor: Yoshinori Kita, Kuki (JP)

(73) Assignee: FUJIKURA KASEI CO., LTD., Tokyo (JP)

( * ) Notice: Subject to any disclaimer, the term of this patent is extended or adjusted under 35 U.S.C. 154(b) by 617 days.

(21) Appl. No.: 16/635,677

(22) PCT Filed: Jul. 10, 2018

(86) PCT No.: PCT/JP2018/026098
§ 371 (c)(1),
(2) Date: Jan. 31, 2020

(87) PCT Pub. No.: WO2019/026569
PCT Pub. Date: Feb. 7, 2019

(65) Prior Publication Data
US 2021/0123907 A1    Apr. 29, 2021

(30) Foreign Application Priority Data

Aug. 1, 2017   (JP) .............................. JP2017-149290
Oct. 27, 2017  (JP) .............................. JP2017-208678

(51) Int. Cl.
| | |
|---|---|
| *G01N 33/531* | (2006.01) |
| *G01N 33/543* | (2006.01) |
| *A61K 8/44* | (2006.01) |
| *G01N 15/00* | (2006.01) |

(52) U.S. Cl.
CPC ............. *G01N 33/531* (2013.01); *A61K 8/44* (2013.01); *G01N 33/54313* (2013.01); *G01N 2015/0092* (2013.01)

(58) Field of Classification Search
CPC ........... G01N 33/531; G01N 33/54313; G01N 2015/0092; G01N 33/54393; A61K 8/44
See application file for complete search history.

(56) References Cited

U.S. PATENT DOCUMENTS

2012/0329986 A1   12/2012   Bolduc et al.

FOREIGN PATENT DOCUMENTS

| EP | 1970704 A1 | 9/2008 |
|---|---|---|
| JP | 61-274261 A | 12/1986 |
| JP | 02-259566 A | 10/1990 |
| JP | 03-084461 A | 4/1991 |
| JP | 09-281103 A | 10/1997 |
| JP | 11-218534 A | 8/1999 |
| JP | 2004-163423 A | 6/2004 |
| JP | 2013-148496 A | 8/2013 |

OTHER PUBLICATIONS

Extended European Search Report from the European Patent Office dated Mar. 23, 2021 in Application No. 18 84 0741.5.
International Preliminary Report on Patentability and Translation of Written Opinion dated Feb. 13, 2020 from the International Bureau in application No. PCT/JP2018/026098.
International Search Report dated Sep. 18, 2018 from the International Bureau in application No. PCT/JP2018/026098.

*Primary Examiner* — Robert S Cabral
(74) *Attorney, Agent, or Firm* — Sughrue Mion, PLLC

(57) ABSTRACT

An object of the present invention is to find a component which can prevent non-specific flocculation of sensitized or unsensitized insoluble carrier particles contained in an immunoassay reagent when the reagent is frozen, to thereby provide means for preventing degradation of the immunoassay reagent. The component which can prevent non-specific flocculation of insoluble carrier particles is the following ω-aminocarboxylic acid (1) [wherein n is an integer of 2 to 6]. The invention provides an immunoassay reagent containing insoluble carrier particles and ω-aminocarboxylic acid (1), and a method for preventing degradation of an immunoassay reagent by using ω-aminocarboxylic acid (1).

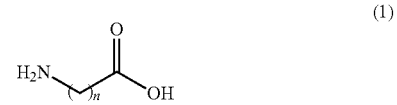

(1)

6 Claims, 31 Drawing Sheets

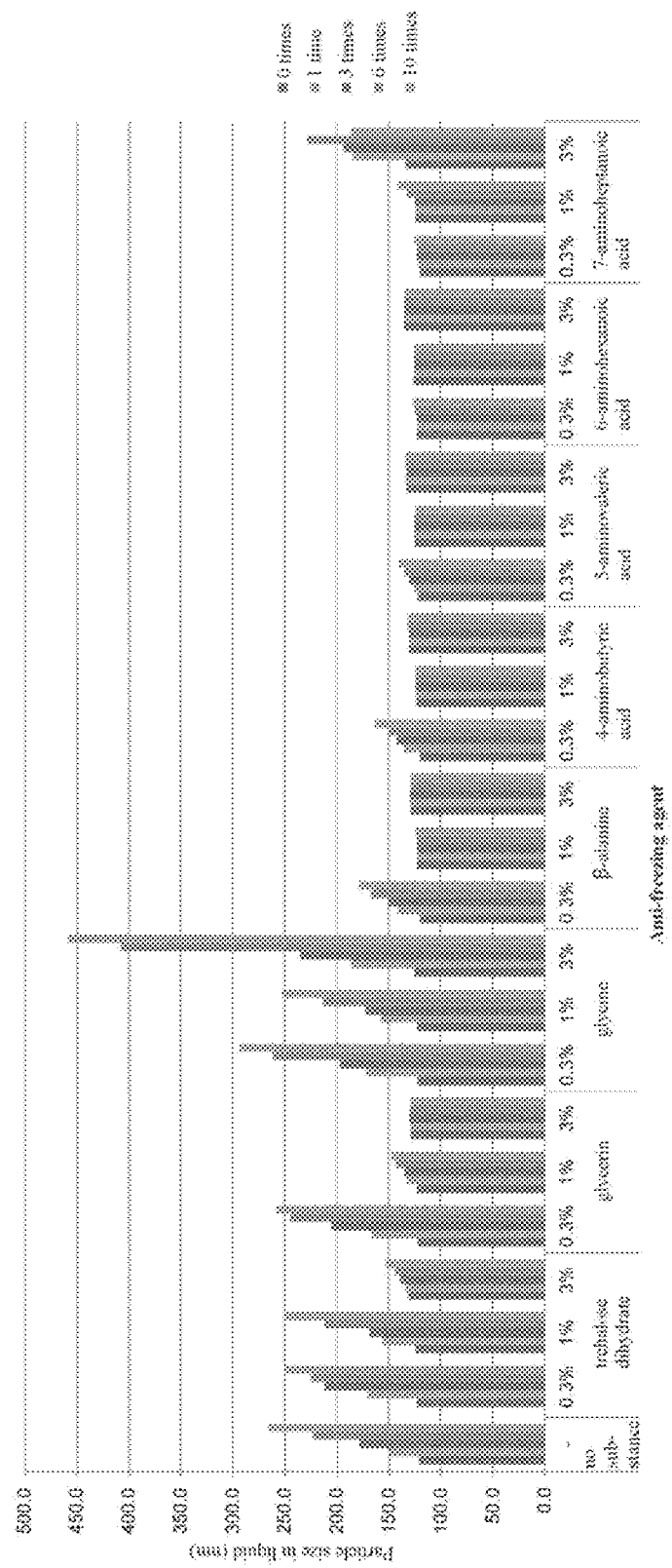
[Fig. 1]

[Fig. 2-1]
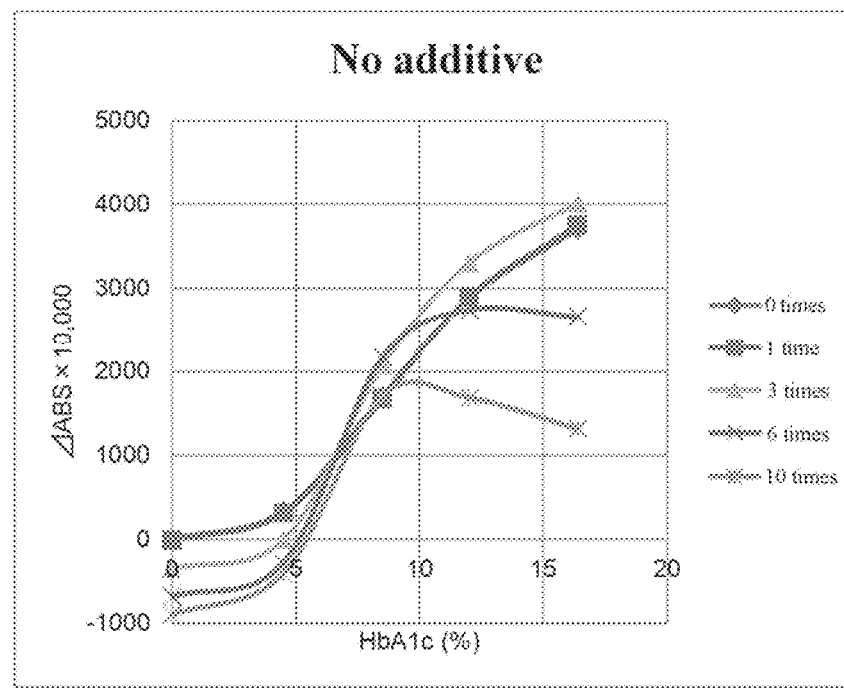

[Fig. 2-2]
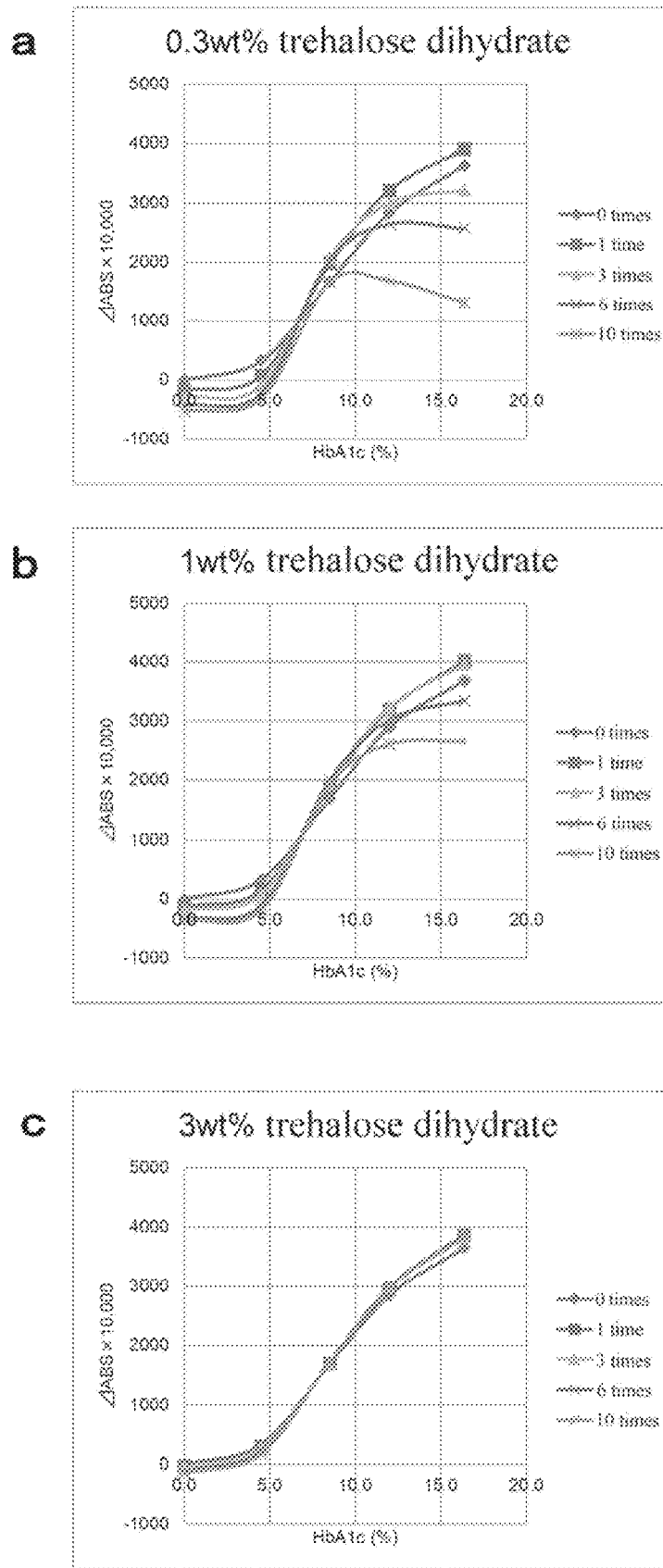

[Fig. 2-3]
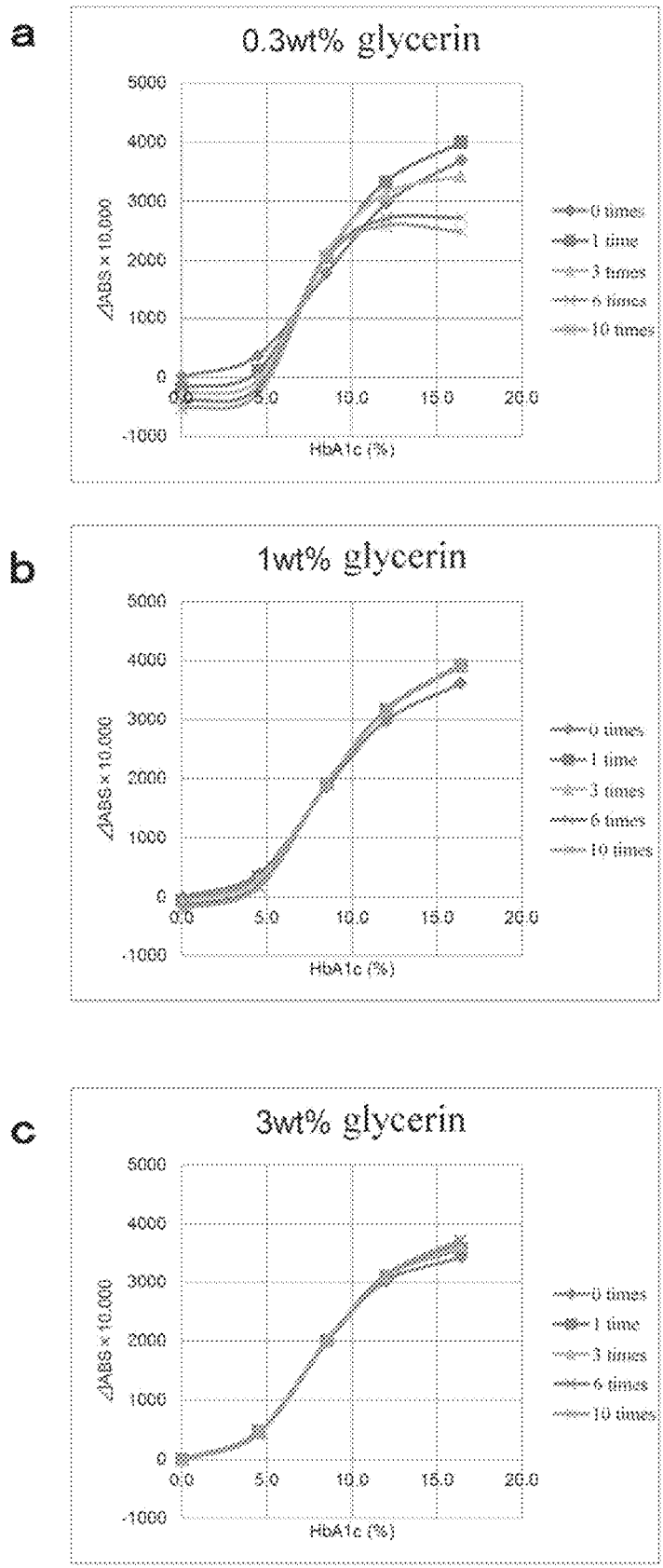

[Fig. 2-4A]
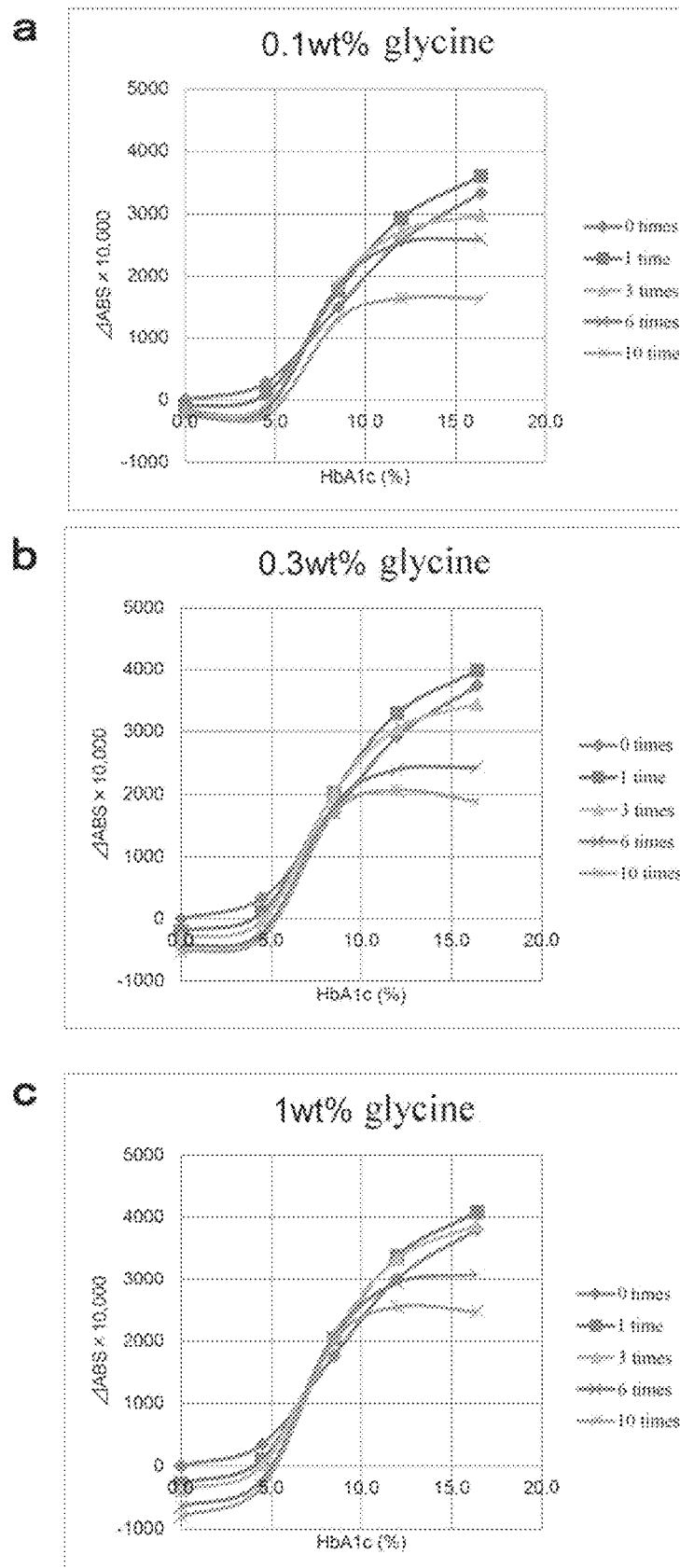

[Fig. 2-4B]
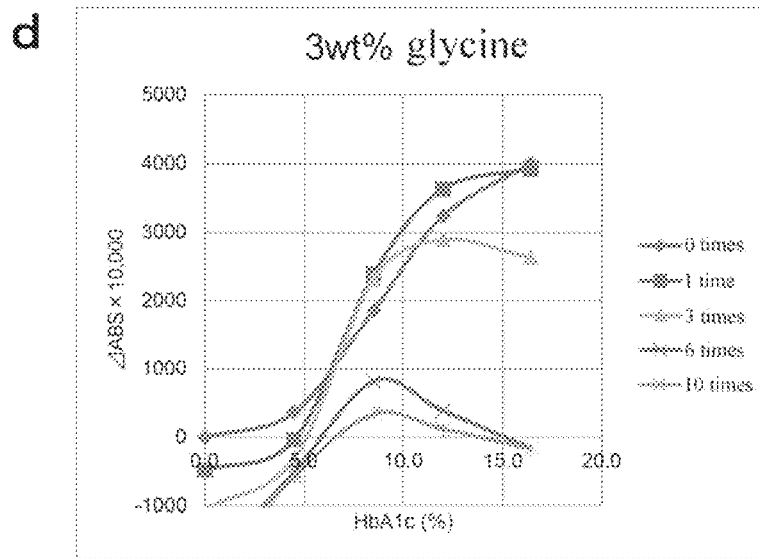
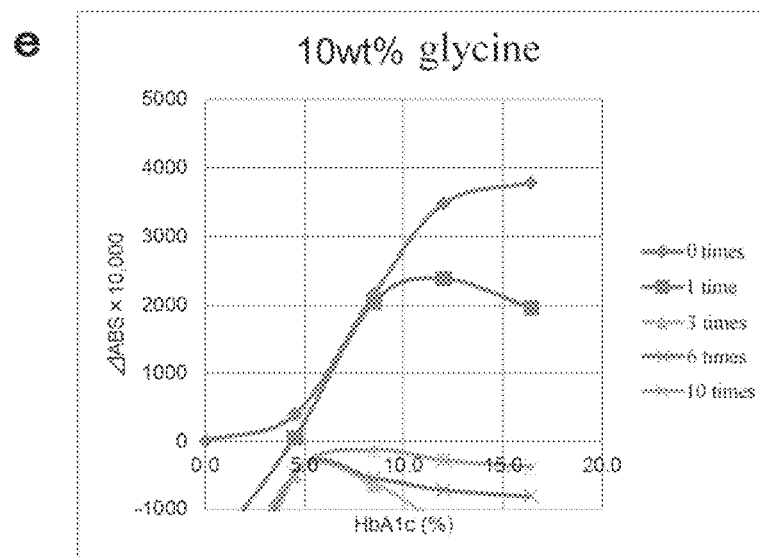

[Fig. 2-5A]
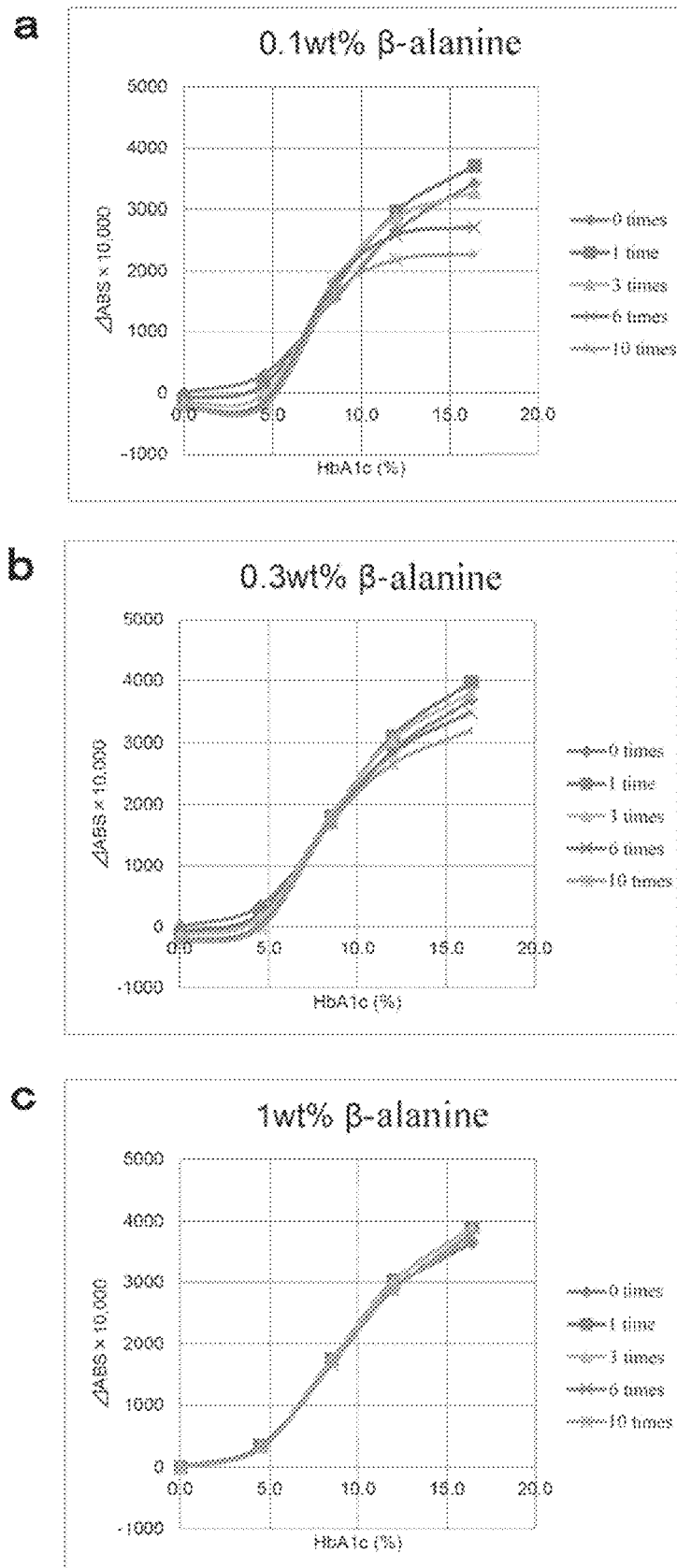

[Fig. 2-5B]
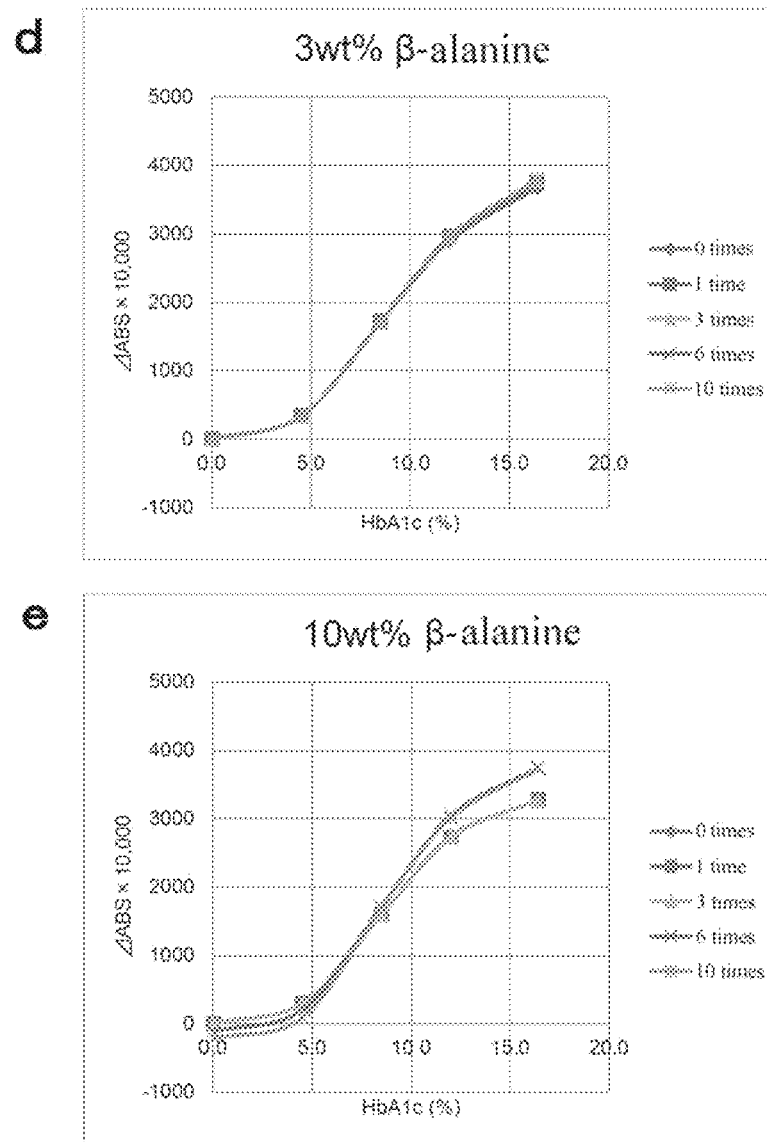

[Fig. 2-6A]
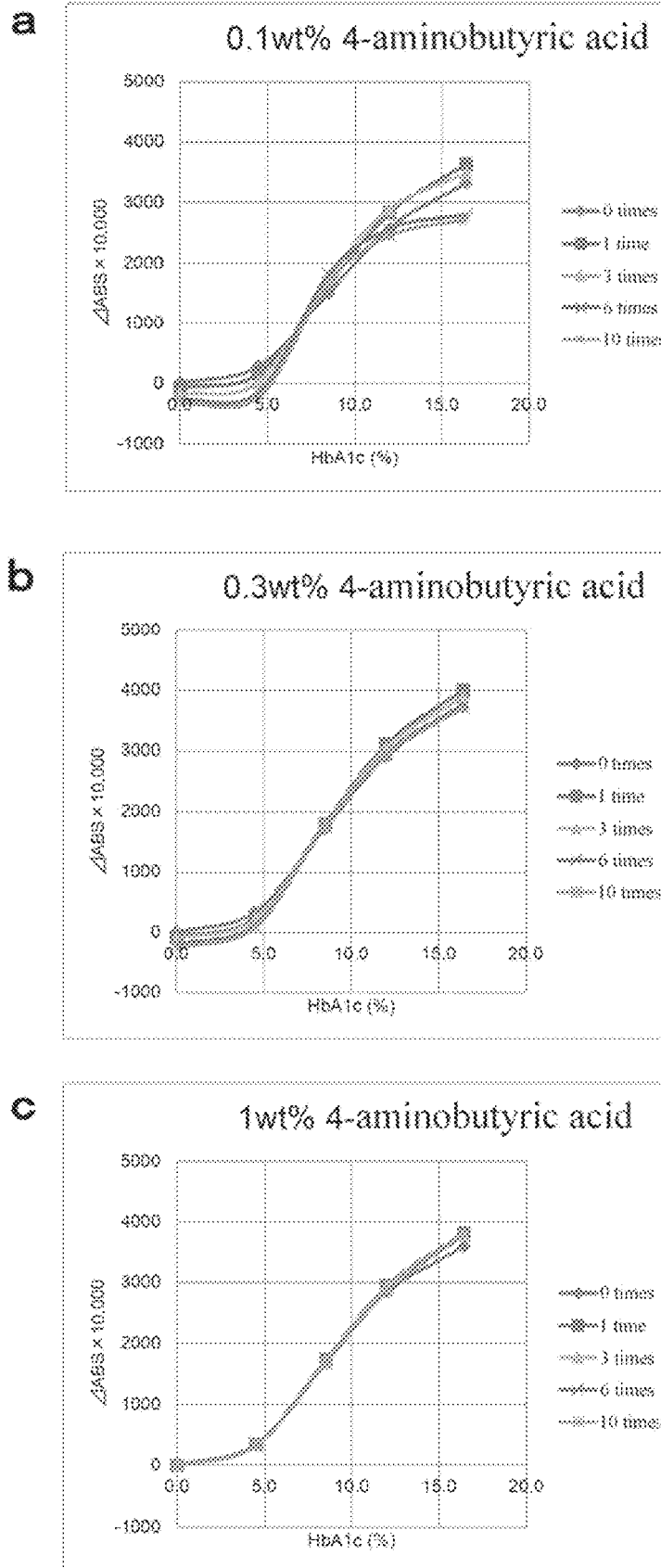

[Fig. 2-6B]
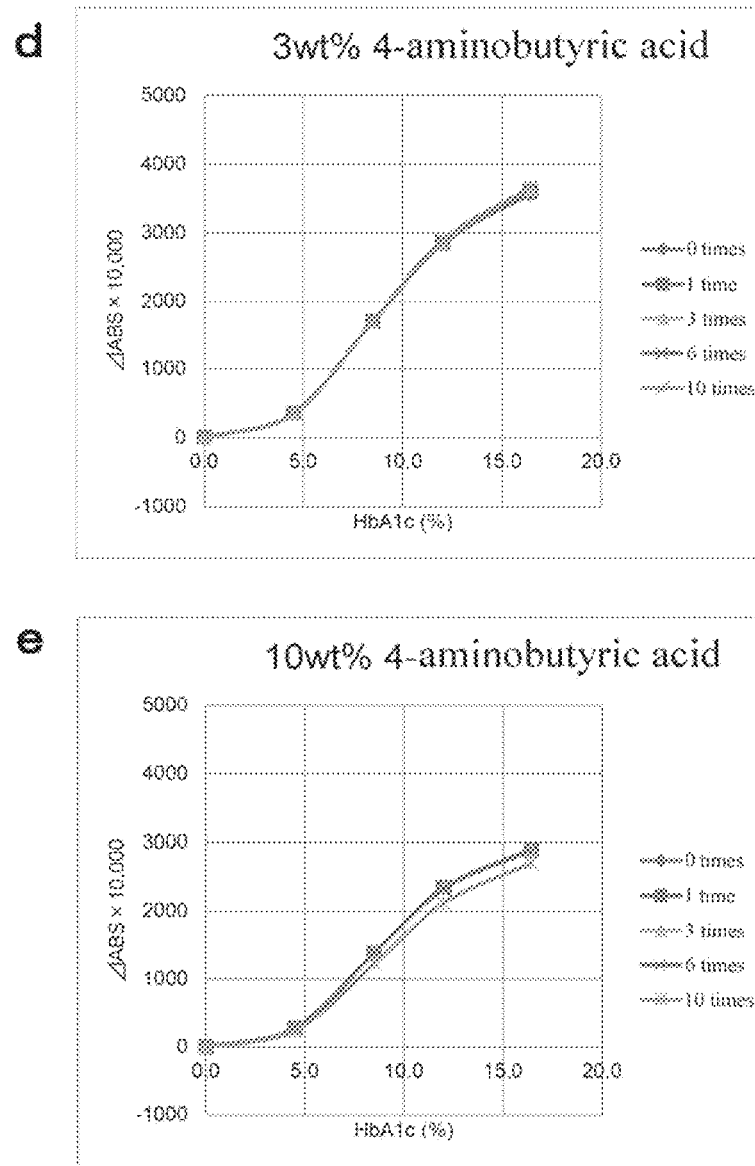

[Fig. 2-7A]
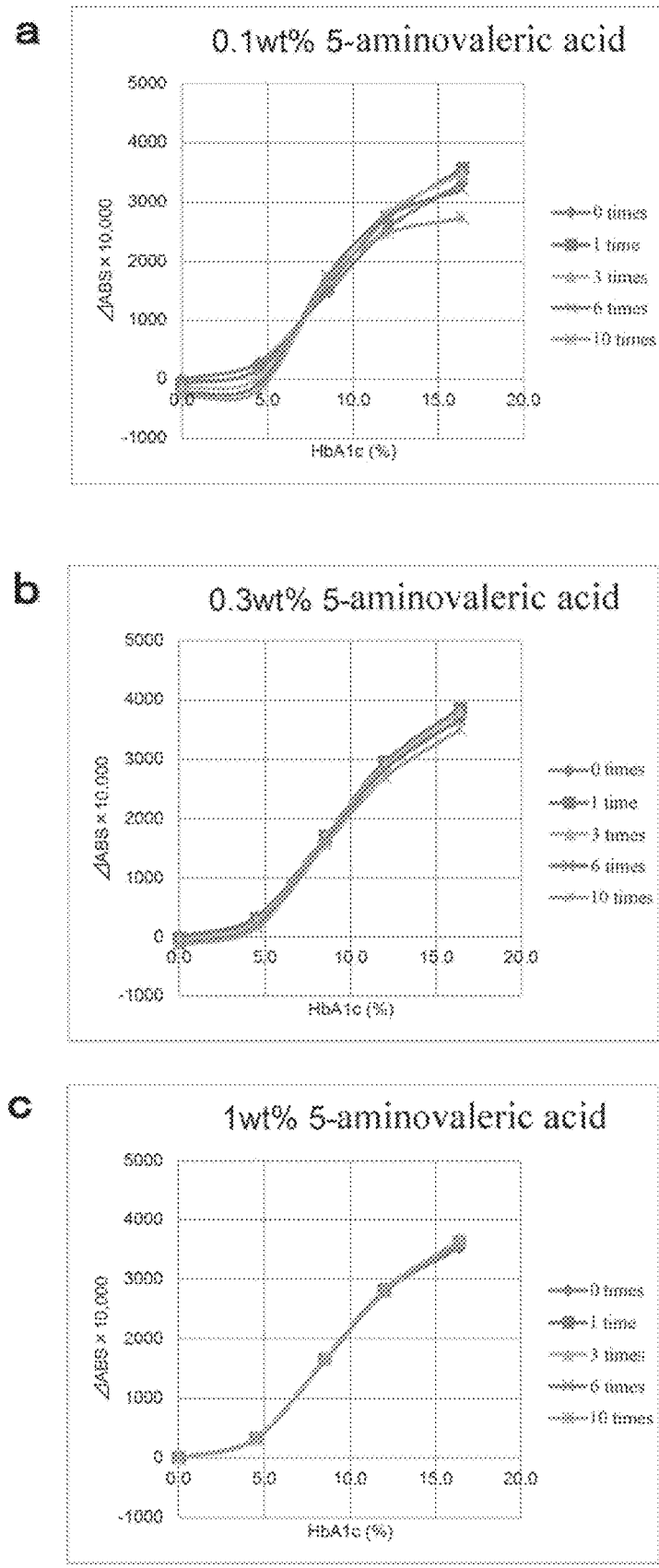

[Fig. 2-7B]
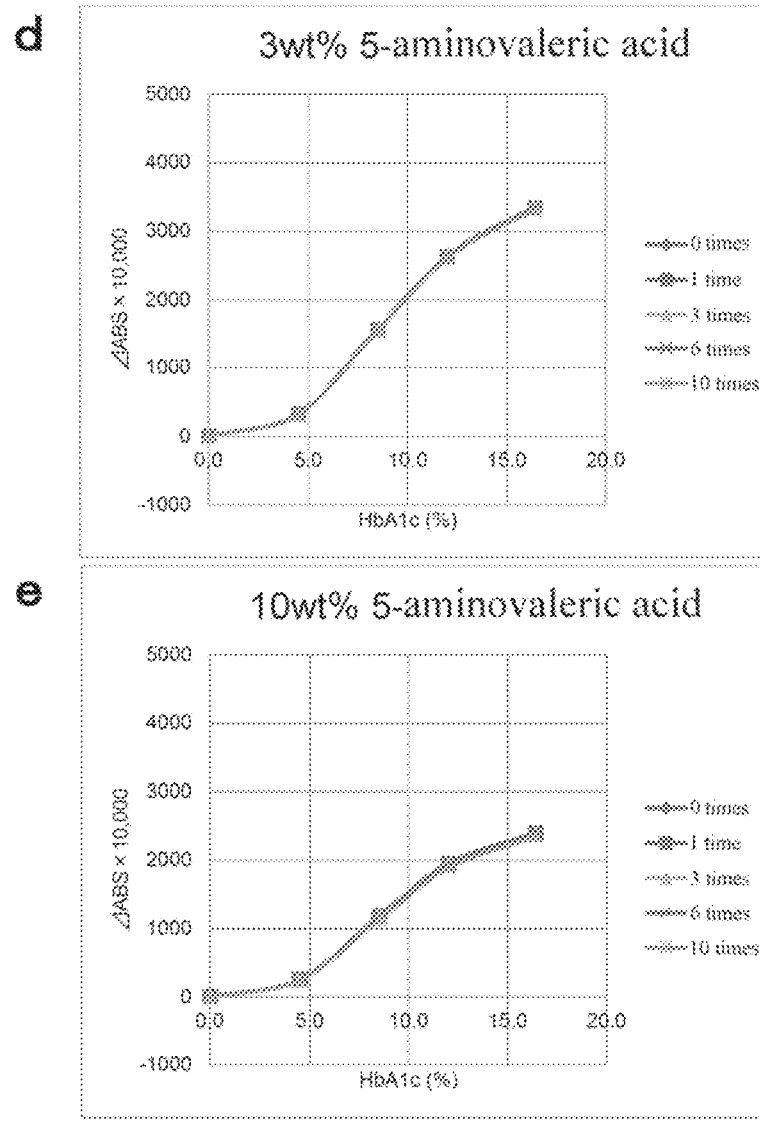

[Fig. 2-8A]
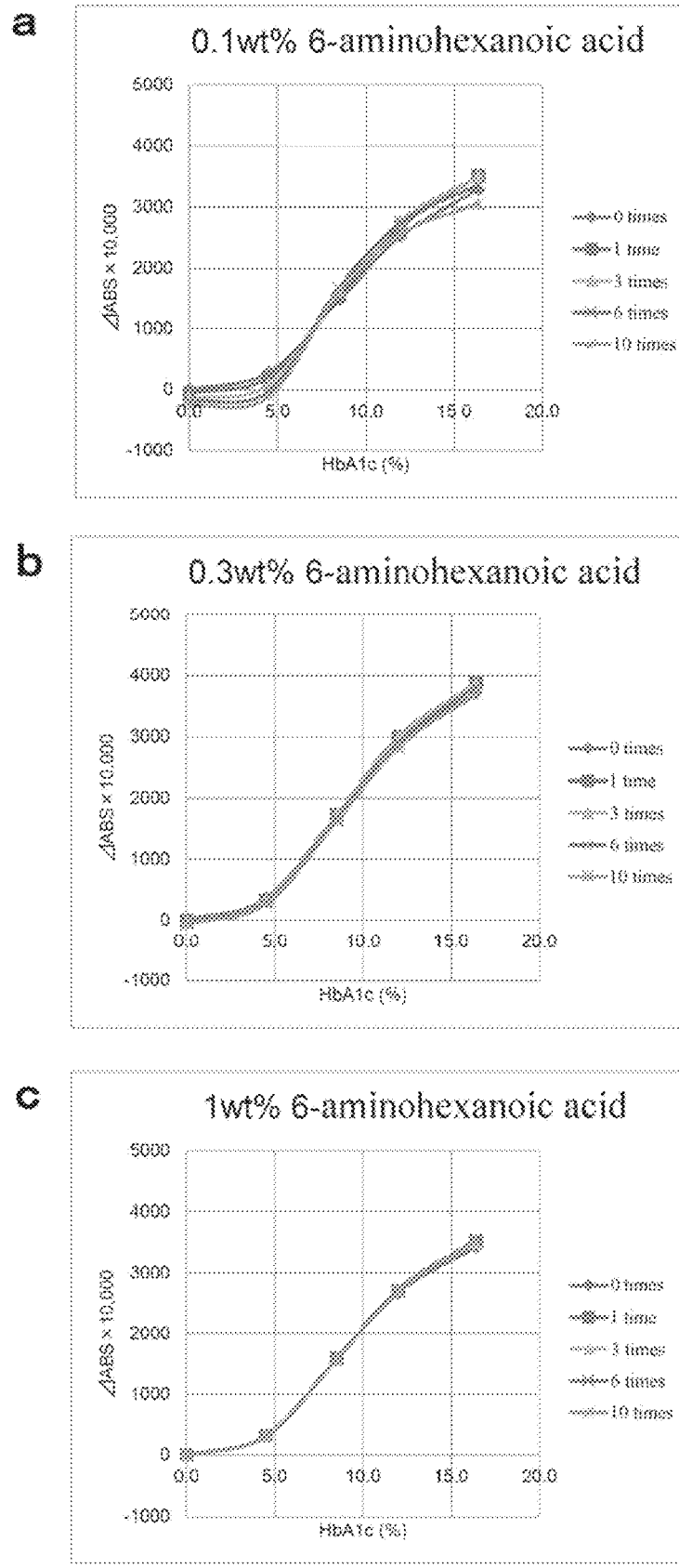

[Fig. 2-8B]
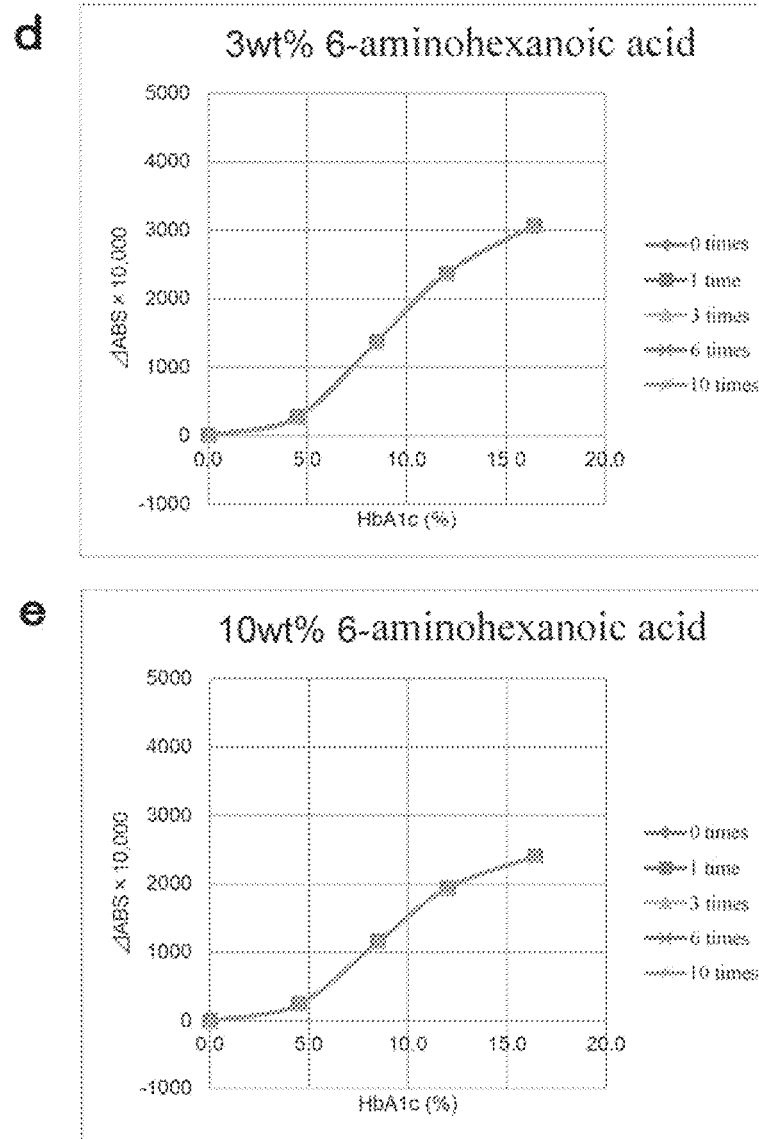

[Fig. 2-9A]
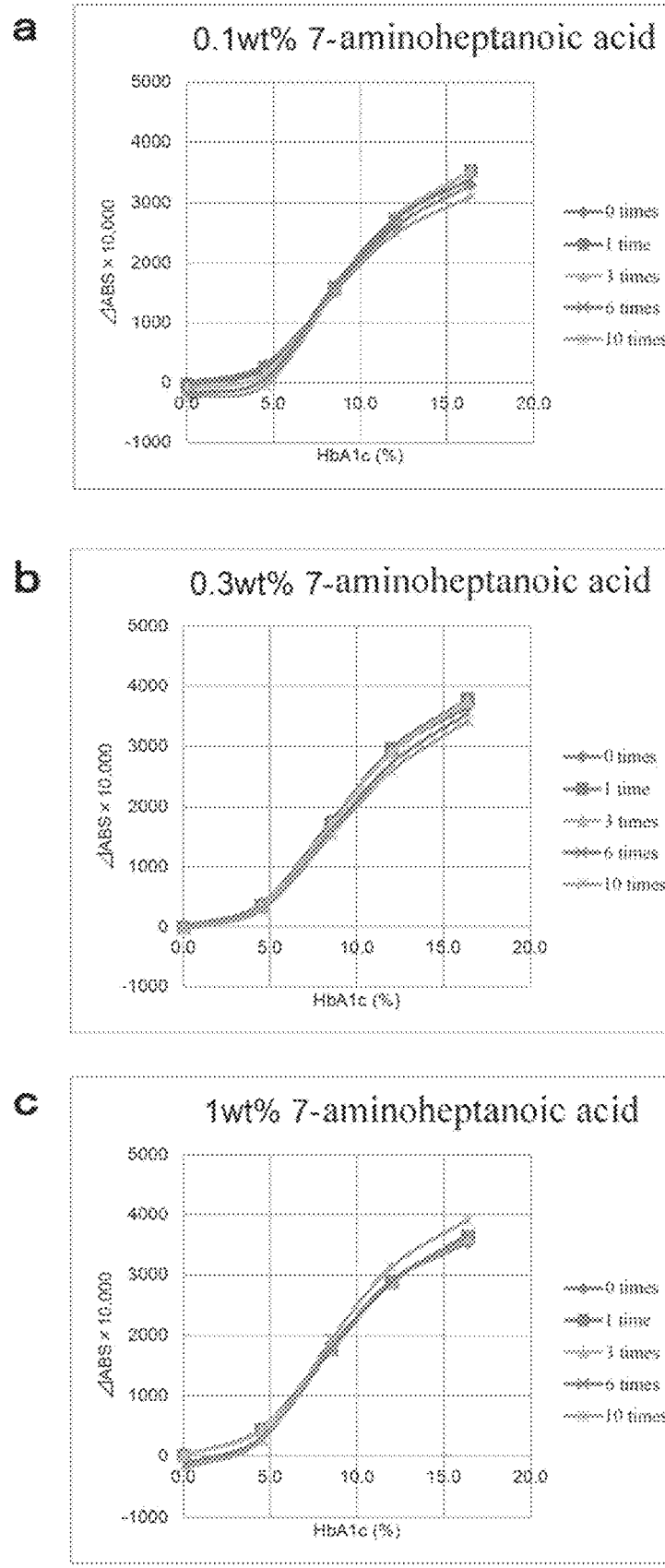

[Fig. 2-9B]
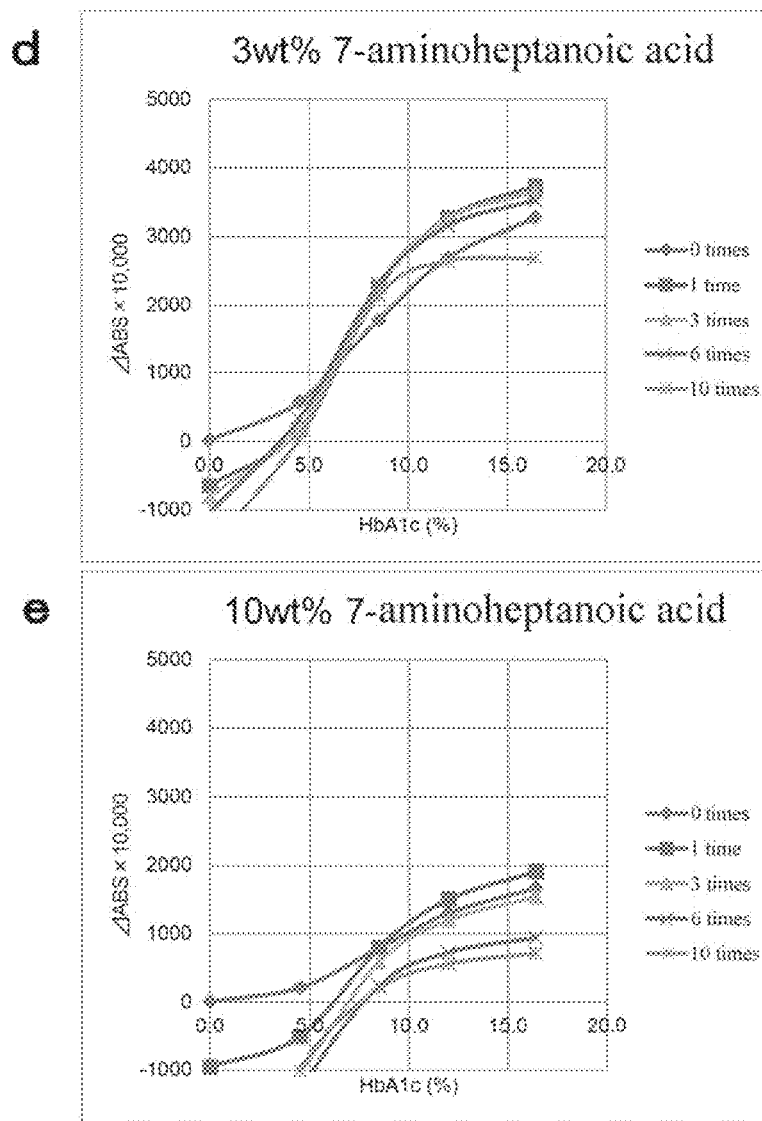

[Fig. 3-1]
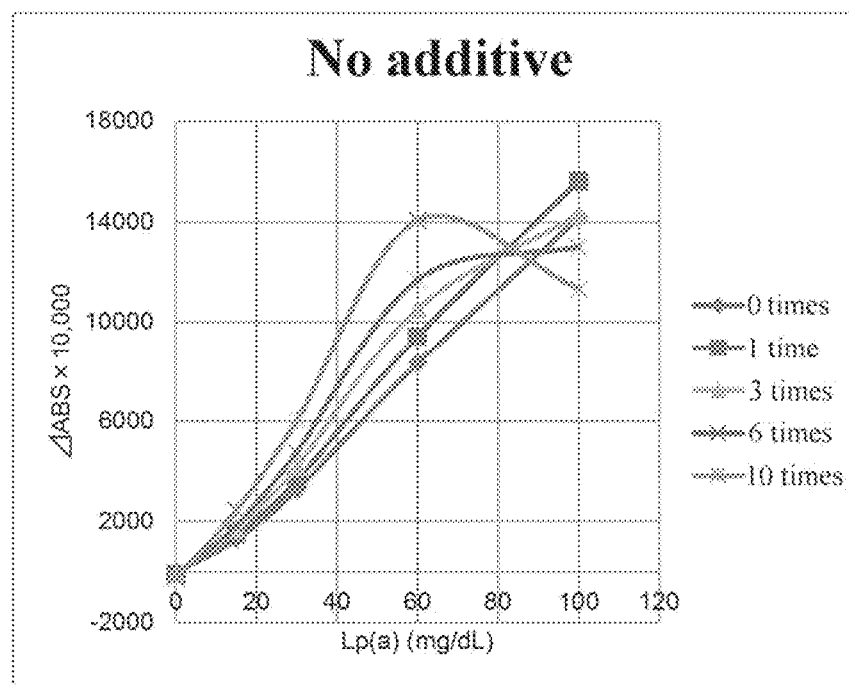

[Fig. 3-2A]
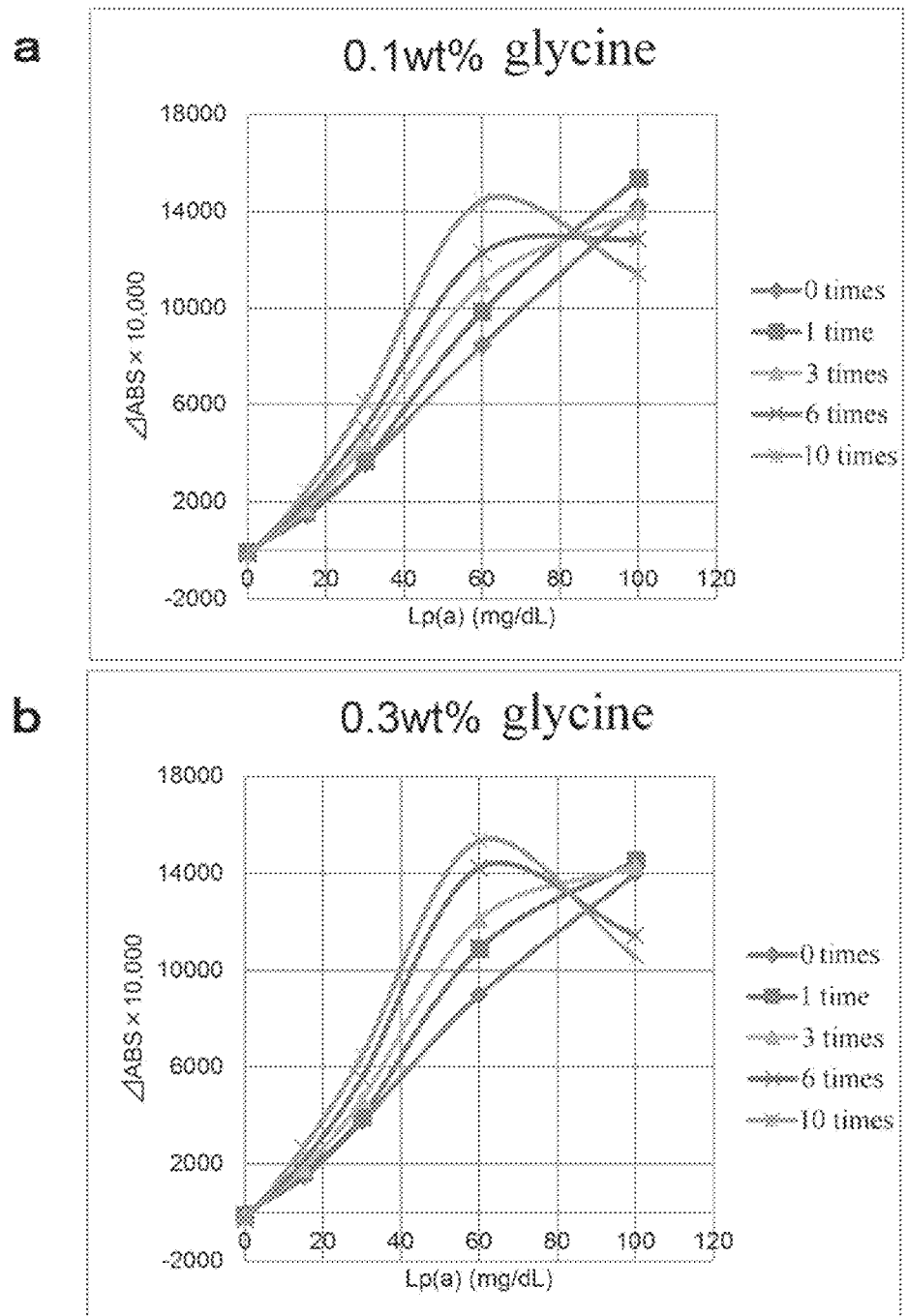

[Fig. 3-2B]
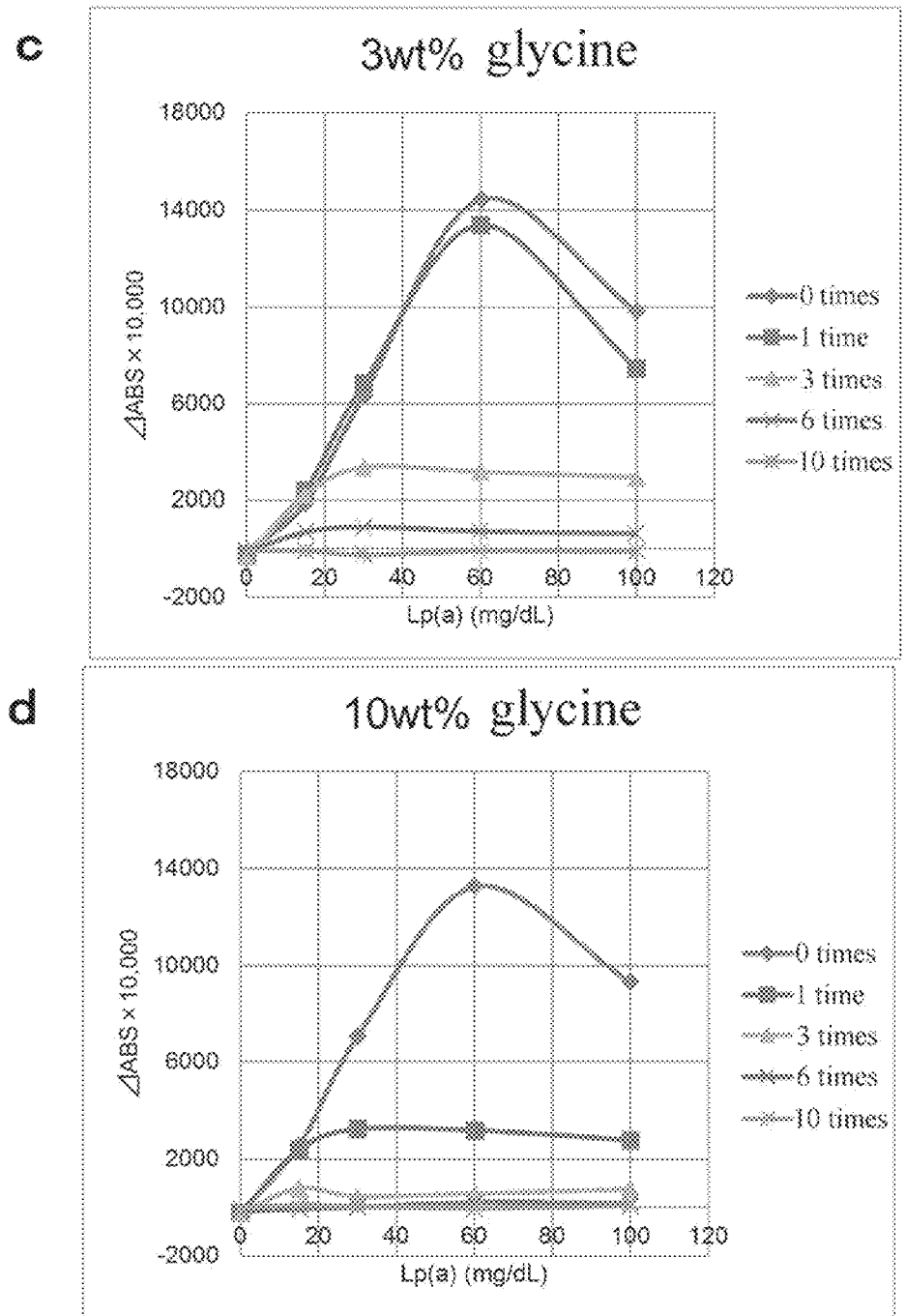

[Fig. 3-3A]
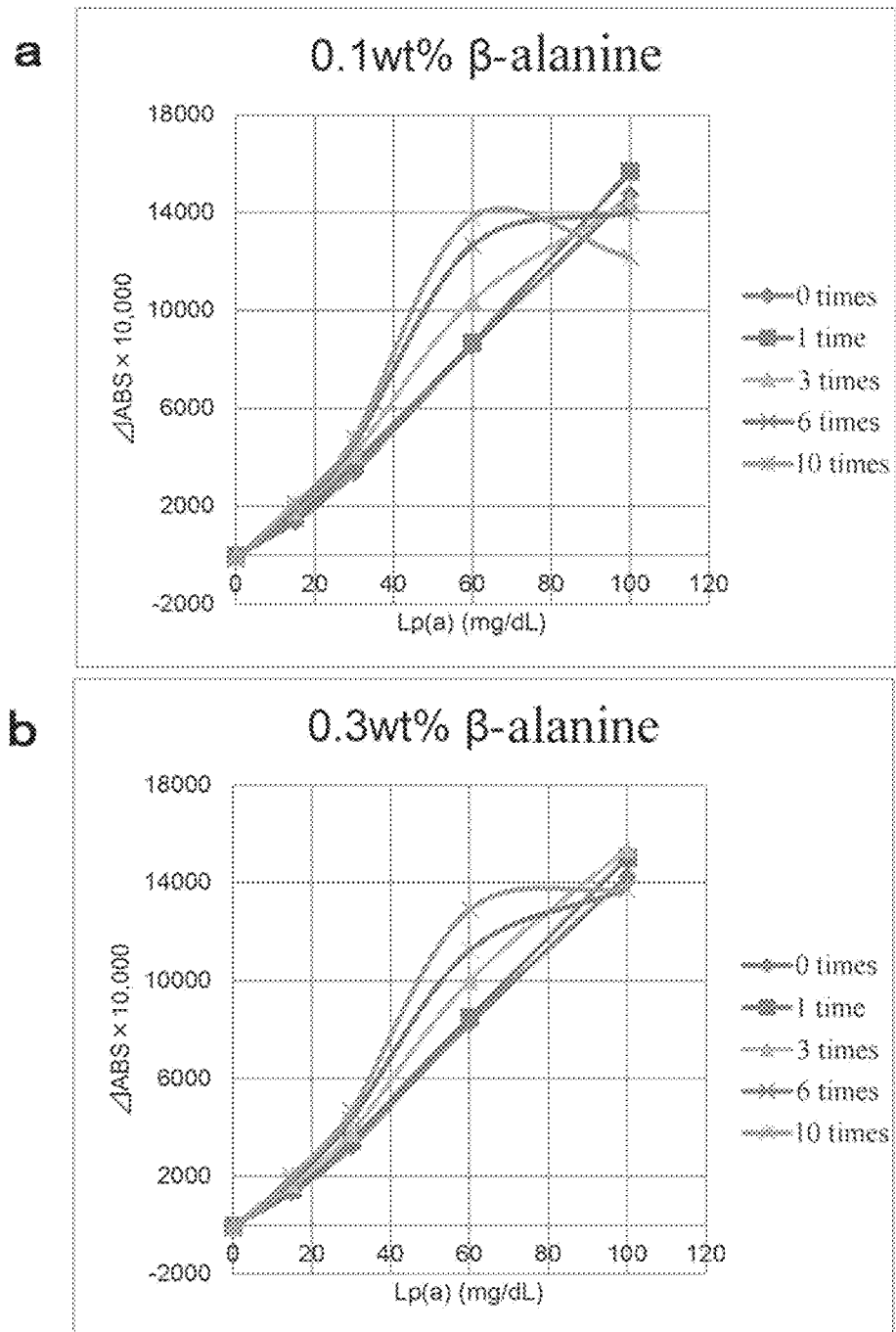

[Fig. 3-3B]
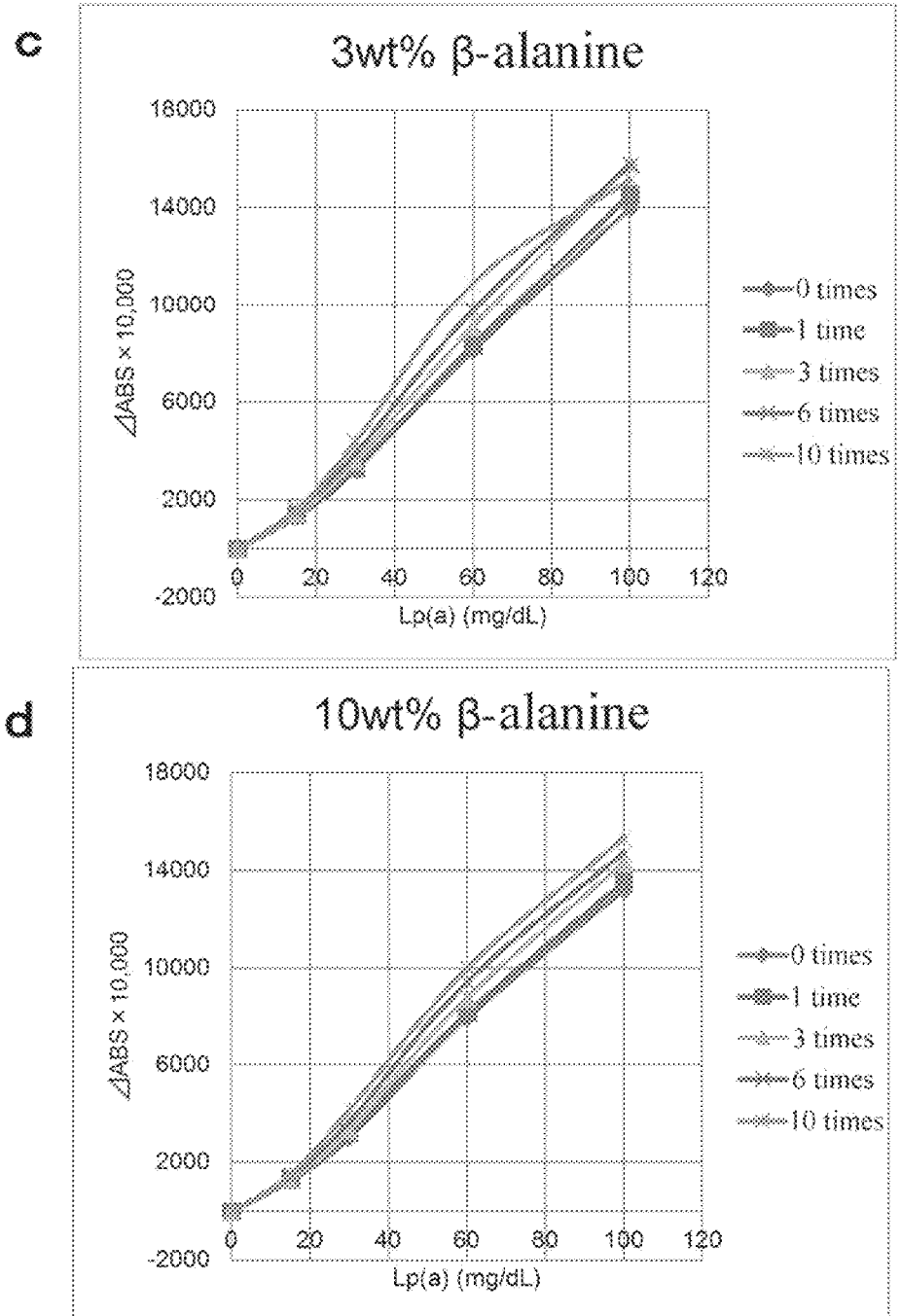

[Fig. 3-4A]
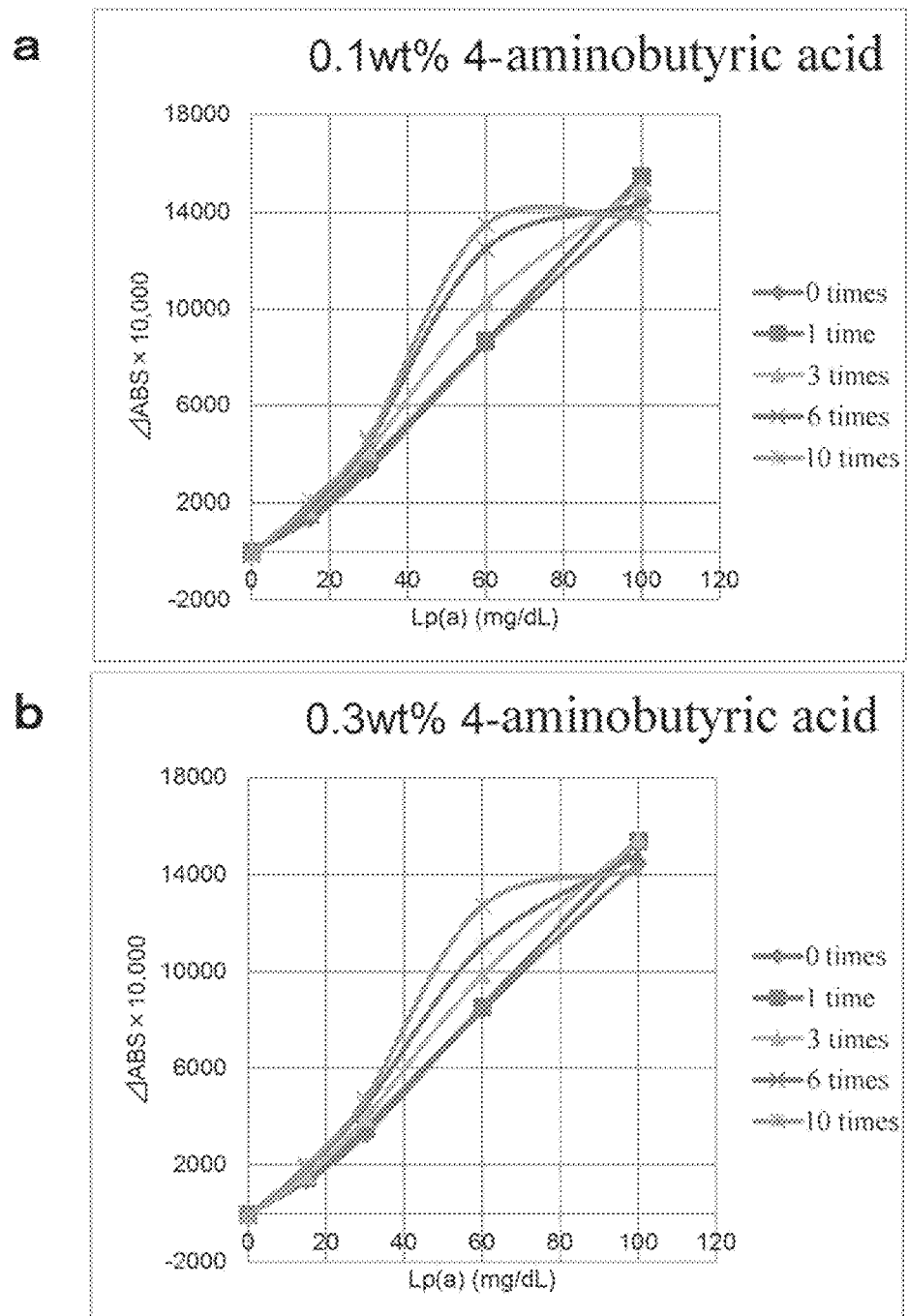

[Fig. 3-4B]
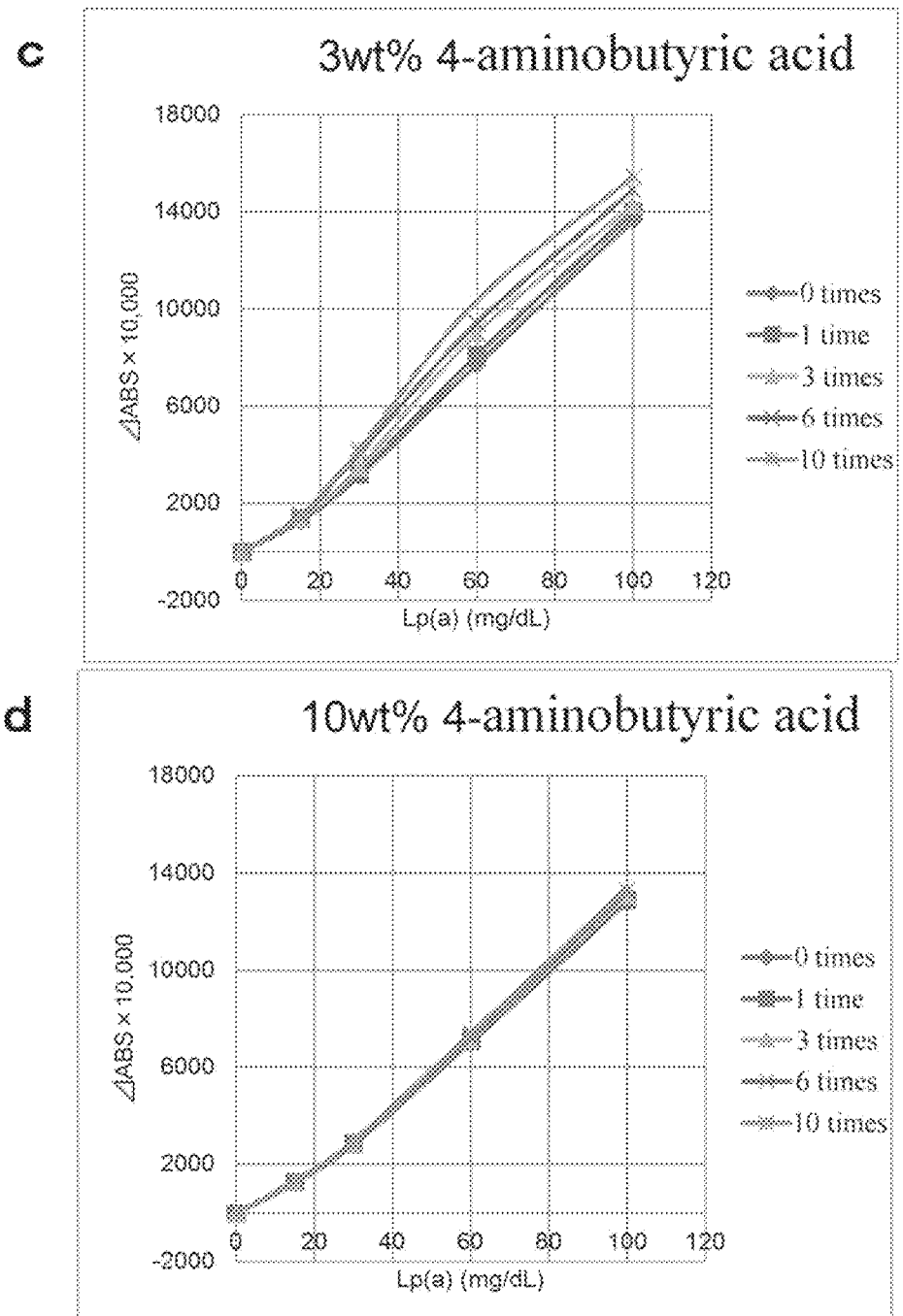

[Fig. 3-5A]
a
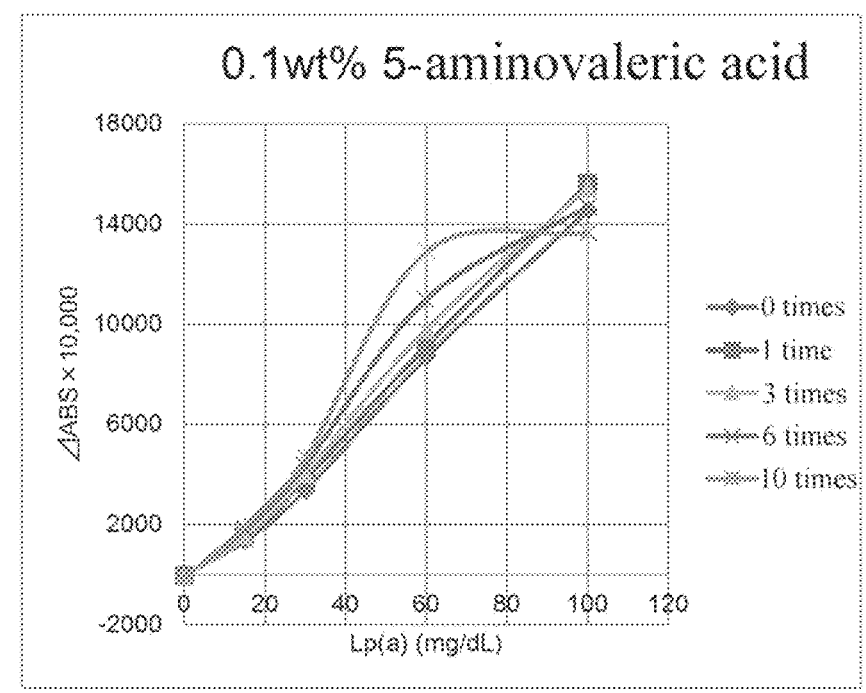
b
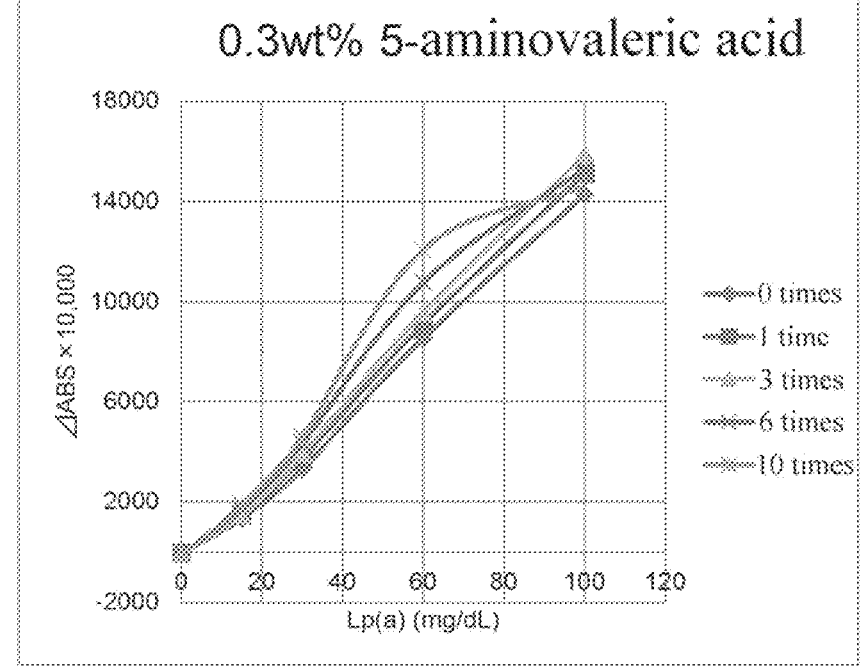

[Fig. 3-5B]
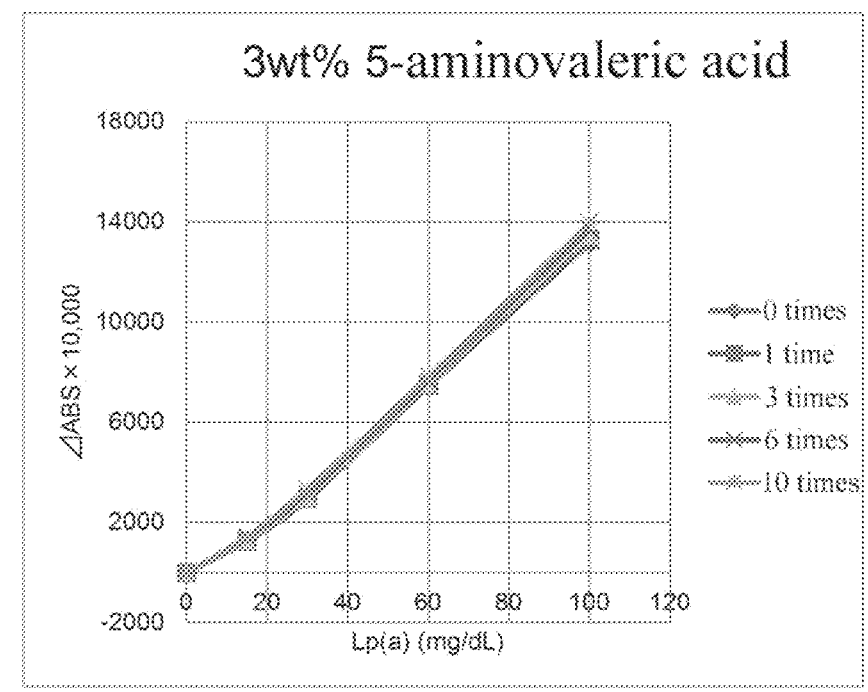
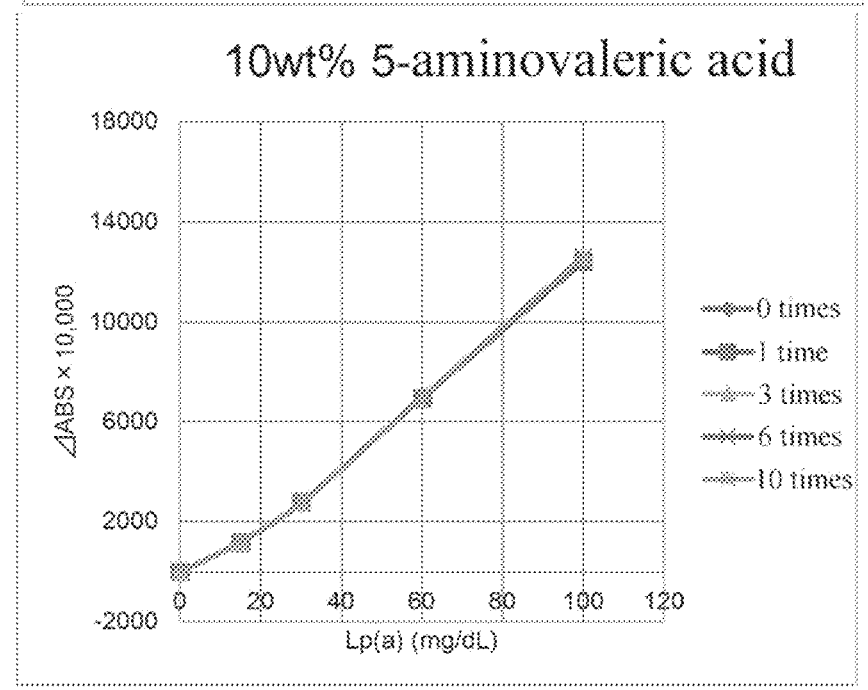

[Fig. 3-6A]
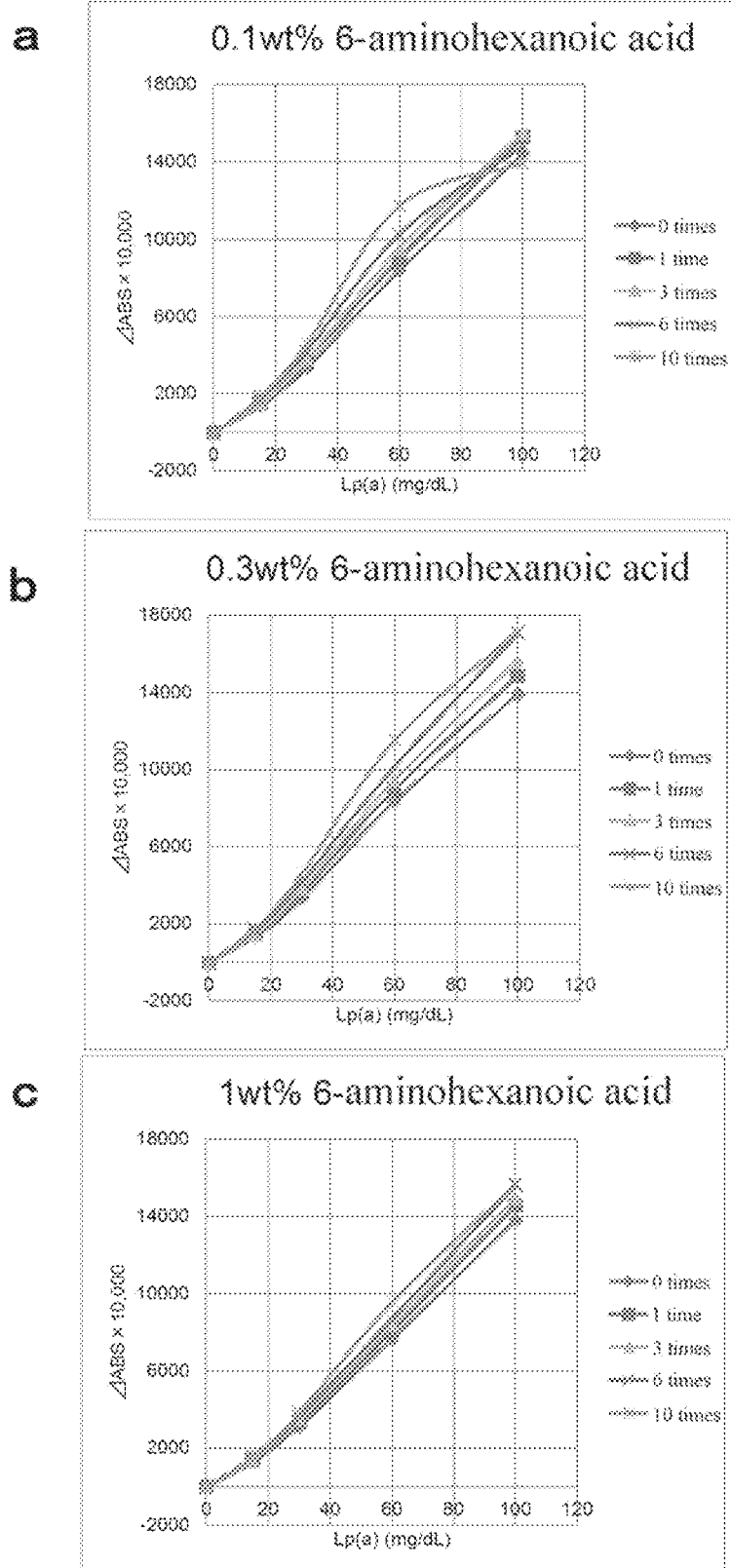

[Fig. 3-6B]
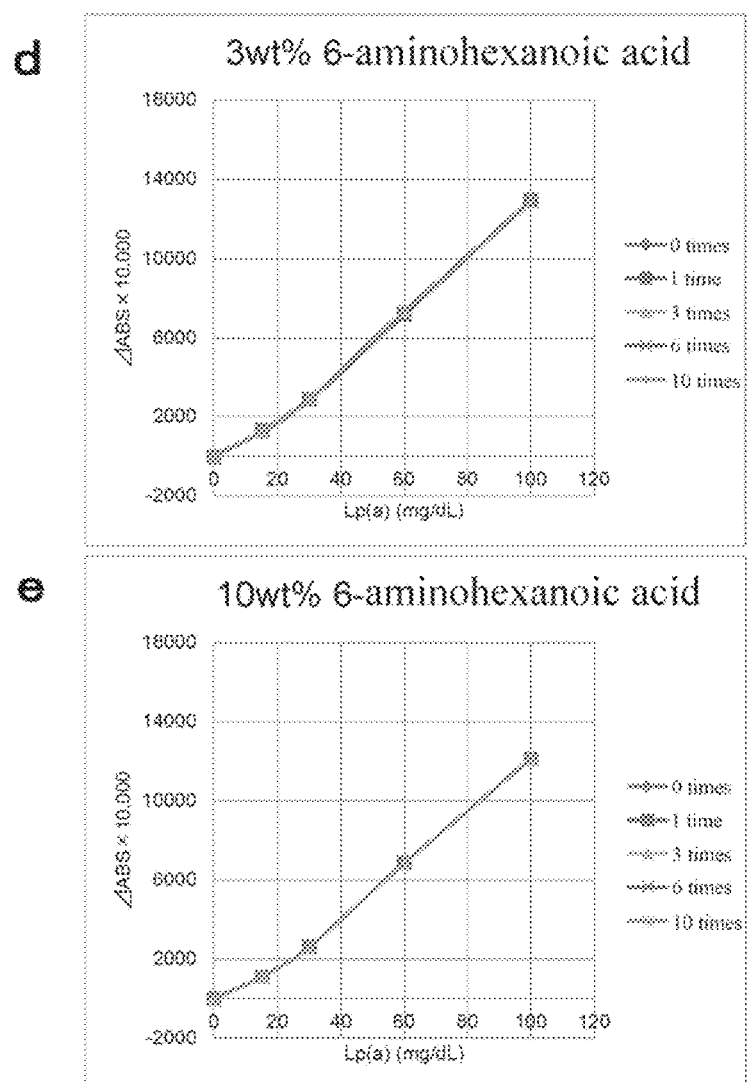

[Fig. 3-7A]
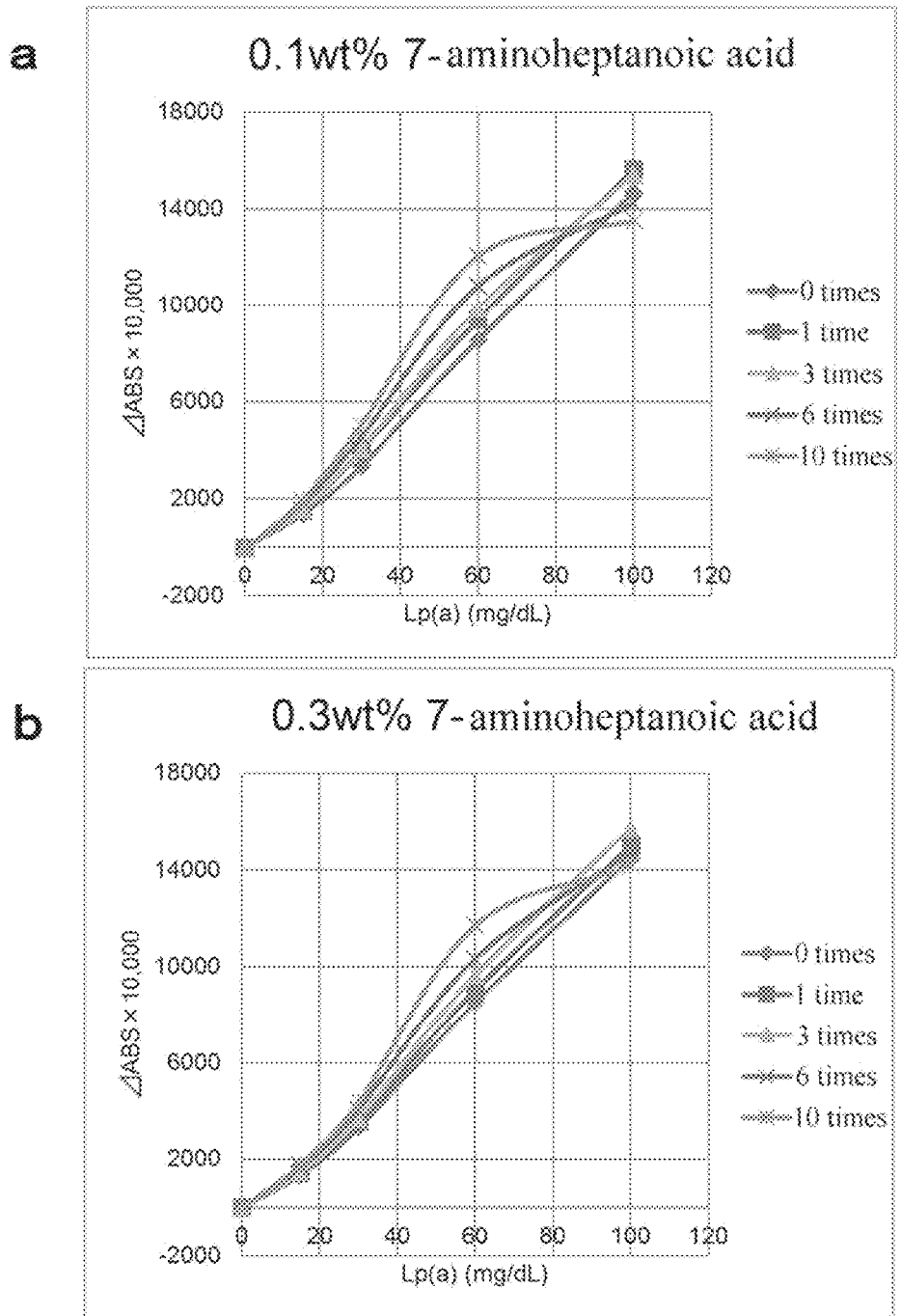

[Fig. 3-7B]
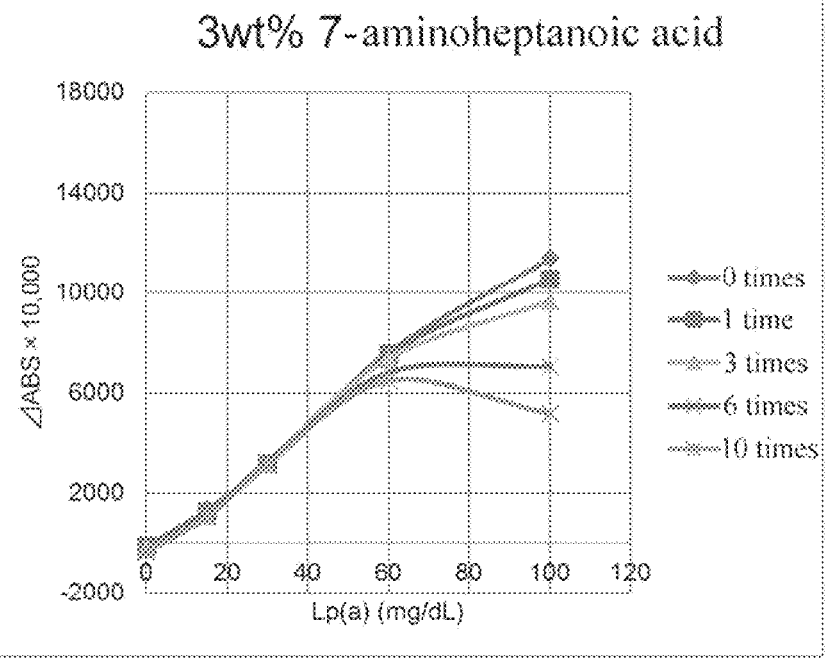
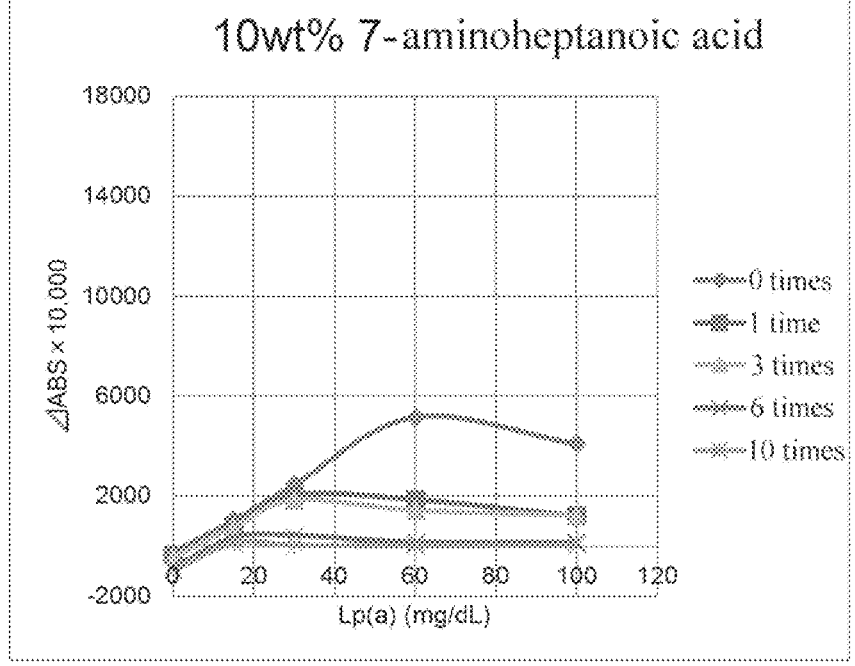

[Fig. 4A]
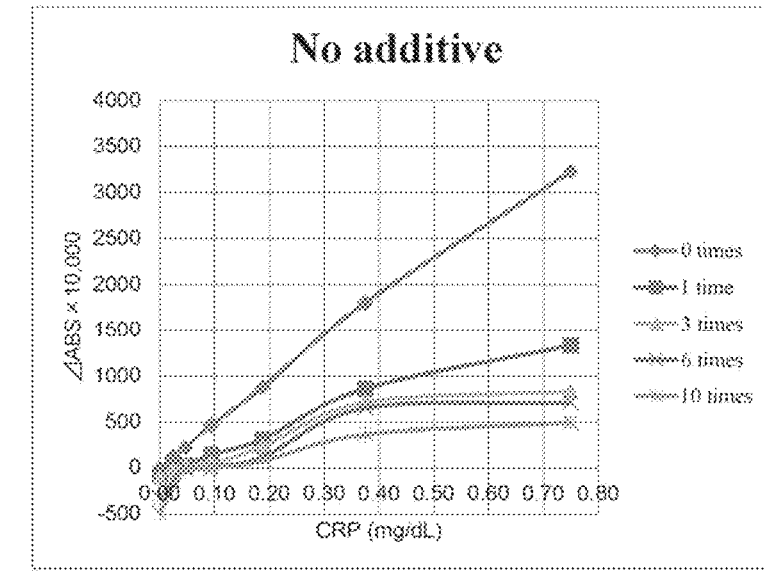
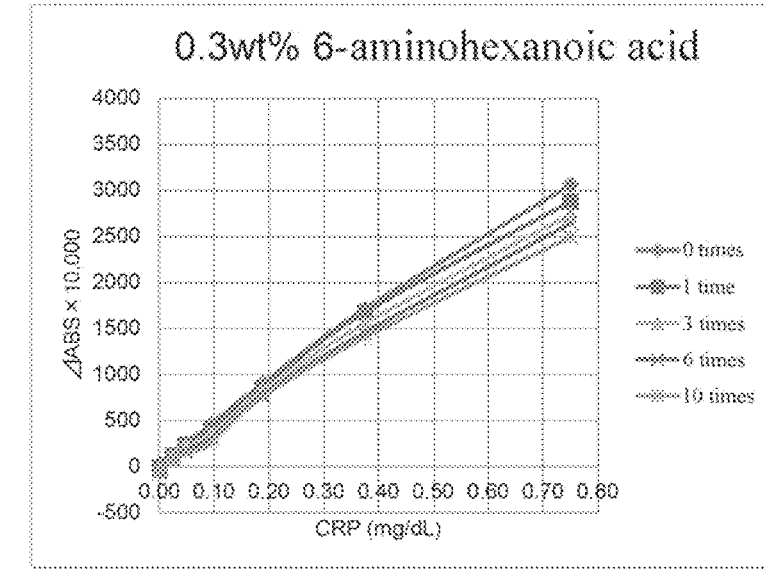

[Fig. 4B]
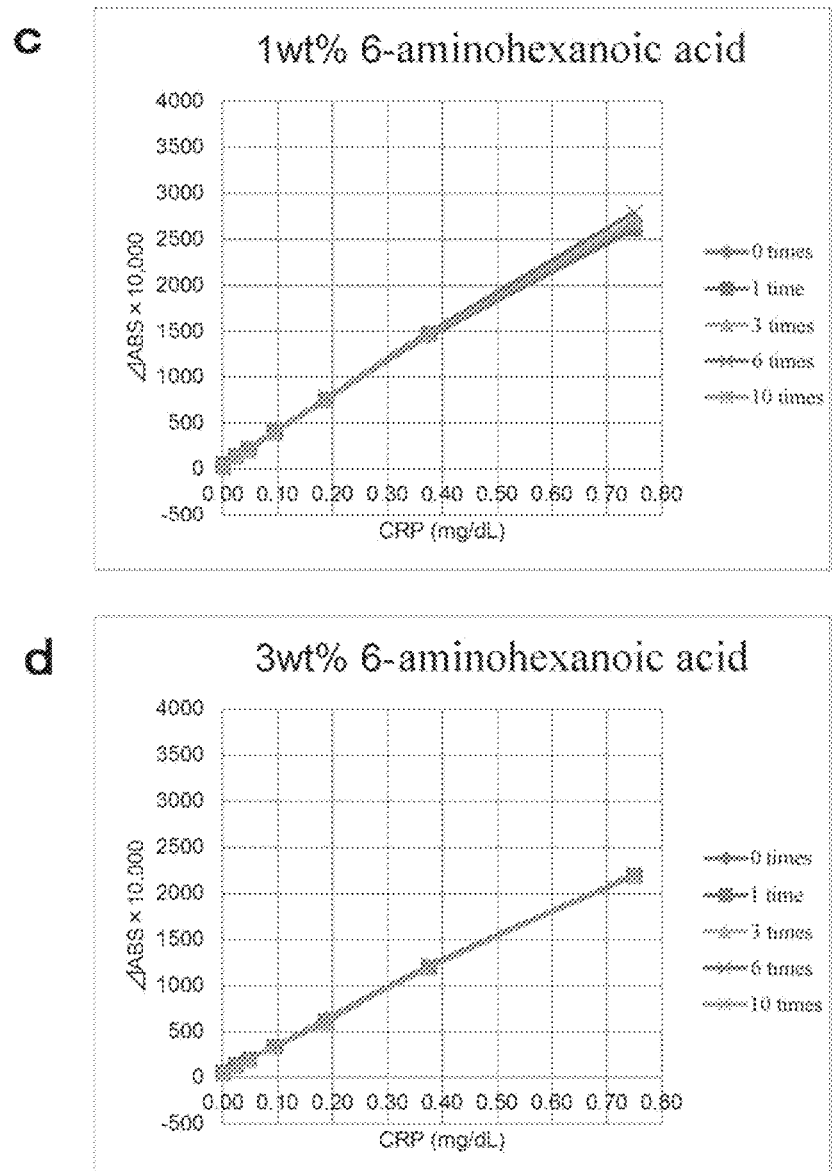

DEGRADATION PREVENTING MEANS FOR IMMUNOASSAY REAGENT CONTAINING INSOLUBLE CARRIER PARTICLES

CROSS REFERENCE TO RELATED APPLICATIONS

This application is a National Stage of International Application No. PCT/JP2018/026098 filed Jul. 10, 2018, claiming priority based on Japanese Patent Application No. 2017-149290 filed Aug. 1, 2017 and Japanese Patent Application No. 2017-208678 filed Oct. 27, 2017.

TECHNICAL FIELD

The present invention relates to means for preventing degradation of an immunoassay reagent containing insoluble carrier particles. According to the present invention, degradation of a liquid-form reagent, which would otherwise be caused by non-specific flocculation of insoluble carrier particles in a freezing/thawing process, can be prevented, regardless of whether the insoluble carrier particles are unsensitized or sensitized. Typical insoluble carrier particles are latex particles and colloidal gold particles.

BACKGROUND ART

Currently, immunoassay reagents containing insoluble carrier particles such as latex particles and colloidal gold particles are widely used in various clinical examinations.

In the case of an immunoassay reagent using a latex agglutination method or a colloidal gold agglutination method, an assay system is formed in which an antibody or an antigen is detected through employing a latex or gold colloid which has been sensitized with an antigen or an antibody or an unsensitized latex or gold colloid in a liquid phase. Based on the property of latex particles and colloidal gold particles agglutinating due to the formation of immune complexes, the immunoassay can be made by determining the degree of agglutination through visual observation or through measurement of an increase in turbidity as a change in absorbance or scattered light intensity.

The latex agglutination method and the colloidal gold agglutination method can be performed in a simple manner and can be relatively easily applied to an automatic analyzer. Thus, these assay techniques are one of the most widely used examination methods at present.

Even though the immunoassay reagent containing insoluble carrier particles such as latex particles and colloidal gold particles is in a freeze-dry form as a commercial product, it is used as a dispersion of the insoluble carrier particles at least upon use. Therefore, the reagent is preferably in a dispersion form in advance, from the viewpoint of ease of handling in actual assay sites.

PRIOR ART DOCUMENTS

Patent Documents

Patent Document 1: WO 2014/132833 pamphlet

SUMMARY OF THE INVENTION

Problems to be Solved by the Invention

Since the immunoassay reagent containing insoluble carrier particles such as latex particles or colloidal gold particles in the aforementioned dispersion form (hereinafter may be referred to as a liquid-form reagent) is generally stored under appropriate cool conditions (i.e., 2 to 8° C.), degradation of the reagent due to freezing barely occurs. However, during transportation or in a refrigerator with insufficient temperature control, the entirety or a part of the liquid-form reagent may freeze due to supercooling or local cooling. When the frozen reagent thaws, non-specific flocculation of insoluble carrier particles problematically occurs. If such non-specific flocculation occurs, the reactivity of the reagent varies, to lose accuracy of assay measurements, which leads to inaccurate diagnostic results. Thus, such non-specific flocculation is not preferred.

Hitherto, degradation of such a liquid-form reagent due to freezing has been generally prevented through addition of an antifreezing alcohol such as glycerin or ethylene glycol, or a sugar such as trehalose. However, effects of the antifreezes are not satisfactory. In recent years, there has been reported a method for effectively preventing freeze degradation (i.e., degradation due to freezing) of an unsensitized latex reagent, the method including adding trimethylglycine (betaine) in an amount of 5 to 30 mass % (Patent Document 1).

Under such circumstances, an object of the present invention is to find a freeze degradation preventing component which can be applied not only to unsensitized insoluble carrier particles but also to sensitized insoluble carrier particles and which exerts the freeze degradation preventing effect in a relatively small amount of use thereof, thereby realizing enhancement of a technique of stabilizing a liquid-form reagent and further improvement thereof.

Means for Solving the Problems

The present inventor has found that the aforementioned object can be attained by use of a specific ω-aminocarboxylic acid as a freeze degradation preventing component.

In a first aspect of the present invention, there is provided an immunoassay reagent comprising, in a solvent, sensitized or unsensitized insoluble carrier particles and an ω-aminocarboxylic acid represented by the following formula (1):

[F1]

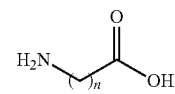

(1)

[wherein n is an integer of 2 to 6]
(hereinafter may be referred to as ω-aminocarboxylic acid (1)). Hereinafter, this immunoassay reagent may be referred to as the "immunoassay reagent of the present invention."

In a second aspect of the present invention, there is provided a method for preventing degradation of an immunoassay reagent, the method comprising causing the aforementioned ω-aminocarboxylic acid (1) to be co-present in an immunoassay reagent comprising sensitized or unsensitized insoluble carrier particles, to thereby prevent non-specific flocculation of the insoluble carrier particles. Hereinafter, this method may be referred to as the "degradation prevention method of the present invention."

As used herein, the term "sensitized" refers to attaching an antigen or an antibody to insoluble carrier particles, or a state in which an antigen or an antibody is attached to insoluble carrier particles. The term "sensitized" has the same meaning as "immobilized on" or "supported on."

The aforementioned immunoassay reagent and the degradation prevention method of the present invention will be described in more detail.

No particular limitation is imposed on the insoluble carrier particles, so long as they can be used for an immunoassay reagent. Examples of the insoluble carrier particles include latex particles; inorganic particles such as silica particles and colloidal gold particles; gelatin particles; and erythrocytes. Of these, latex particles and colloidal gold particles are typically used as the insoluble carrier particles.

The term "latex" is also called "polymer emulsion" and is a dispersion of a polymer which is dispersed in an aqueous solvent such as water. In the dispersion, the aqueous solvent serves as a continuous phase, and particles of the polymer having a spherical or quasi-spherical shape serve as a dispersion phase. The term "latex particles" refers to the polymer particles of the dispersion phase of the latex. As used herein, also, the term "latex" may refer to latex particles.

No particular limitation is imposed on the type of latex, so long as the latex can be used for an immunoassay reagent as mentioned above. Examples of the latex include physical adsorption latexes such as polystyrene latex, ultra-low-carboxylic acid-modified latex, and hydrophilic group-localized latex; chemical bonding latexes such as carboxylic acid-modified latex, amino-modified latex, hydroxy-modified latex, glycidyl-modified latex, aldehyde-modified latex, and amido-modified latex; various colored latexes; latexes for blood agglutination such as high-density polystyrene latex; and magnetic latex.

The term "gold colloid" refers to a dispersion of microparticles to which gold atoms are bonded, and is synthesized through a method such as reduction of tetrachloroauric(III) acid in liquid. In the synthetic process, $Au^{3+}$ ions are reduced to gold atoms, which are bonded to one another. After becoming supersaturated, nucleus particles having a particle size of 1 nm are formed, and the unbound gold atoms are successively bonded to the nucleus particles, to thereby allow particle growth. Through carrying out sufficient stirring in the synthetic step, the particle size can be made uniform. In order to prevent flocculation of microparticles (colloidal gold particles), a stabilizer such as citric acid is generally added. However, the gold colloid tends to intrinsically undergo flocculation.

Generally, gold colloid assumes various colors based on surface plasmon resonance. A monodisperse gold colloid having a uniform particle size exhibits a single absorption wavelength.

The particle size of the colloidal gold particles present in the gold colloid is smaller than that of the aforementioned latex particles, and the specific surface area of the colloidal gold particles with respect to unit weight is large. Thus, the colloidal gold particles are suited for determination of a substance present at high concentration.

The term "sensitized insoluble carrier particles" refers to insoluble carrier particles whose surfaces are sensitized with a certain substance; more specifically to insoluble carrier particles sensitized with an antibody or an antigen for inducing antigen-antibody reaction essential for immunoassay. The antibody may be a monoclonal antibody or a polyclonal antibody. Furthermore, so long as antigen-antibody reaction with the target antigen can be induced, the antibody may be the entirety or a part of an immunoglobulin molecule. No particular limitation is imposed on the antigen, so long as it can bind to the target antibody via antigen-antibody reaction. The term "unsensitized insoluble carrier particles" refers to insoluble carrier particles not sensitized with such an antibody or antigen.

The aqueous solvent is a solvent mainly composed of water, and examples thereof include water and various buffers. The ω-aminocarboxylic acid (1) may be synthesized through a known method, for example, amidation of an α-halocarboxylic acid having a specific number of carbon atoms. Alternatively, a commercial ω-aminocarboxylic acid may also be used. No particular limitation is imposed on the form of the immunoassay reagent, so long as insoluble carrier particles are actually contained and occurrence of flocculation of the particles in a period other than immunoassay affects the immunoassay values. It is preferably an "immunoassay reagent employing an agglutination method" in which the degree of agglutination of the insoluble carrier particles is used as an index for the target antigen-antibody reaction. Examples of the agglutination method include a slide test method, an optical measurement method, a microtiter method, and a filter-separation method. Examples of methods other than the agglutination method include a sandwich method, an immunochromatographic method, and a western blotting method. No particular limitation is imposed on the label employed in the immunoassay, and examples include a radioisotope, a fluorescent substance, a coloring substance, a color developing enzyme, and biotin. As an assay technique employing unsensitized insoluble carrier particles, a method is known in which unsensitized latex particles are brought into contact with a specimen (i.e., an isolated bio-sample), to thereby cause an assay target protein to be adsorbed onto the particle surface; an antibody against the target protein is reacted with the adsorbed protein, to thereby cause agglutination of the particles; and the turbidity of the reaction mixture is measured to determine a target protein amount (Japanese Patent No. 2677753). The present invention is also applicable to an immunoassay reagent based on such a technique using unsensitized insoluble carrier particles.

Effects of the Invention

The present invention provides means for preventing degradation of an immunoassay reagent containing insoluble carrier particles such as latex particles and colloidal gold particles, due to non-specific flocculation of the particles caused by freezing/thawing, as an "immunoassay reagent" and a "method for preventing degradation of an immunoassay reagent." The degradation preventing component of the present invention, which is the ω-aminocarboxylic acid (1), can prevent non-specific flocculation of insoluble carrier particles due to freezing/thawing by incorporation thereof in a relatively small amount, regardless of whether the insoluble carrier particles are sensitized or unsensitized, whereby degradation of the immunoassay reagent can be prevented.

BRIEF DESCRIPTION OF THE DRAWINGS

FIG. 1

Graph showing the particle size changes of unsensitized latex reagents with respect to the number of freezing/thawing operations (0, 1, 3, 6, and 10).

FIG. 2-1

Graph showing non-specific flocculation of latex particles in unsensitized latex reagents in the absence of an additive, with respect to the number of freezing/thawing operations (0, 1, 3, 6, and 10).

FIG. 2-2

Graphs showing non-specific flocculation of latex particles in unsensitized latex reagents in the presence of trehalose dihydrate as an additive, with respect to the number of freezing/thawing operations (0, 1, 3, 6, and 10). In the figure, "a" corresponds to a case of addition of 0.3 mass % trehalose dihydrate, "b" a case of addition of 1 mass % trehalose dihydrate, and "c" a case of addition of 3 mass % trehalose dihydrate.

FIG. 2-3

Graphs showing non-specific flocculation of latex particles in unsensitized latex reagents in the presence of glycerin as an additive, with respect to the number of freezing/thawing operations (0, 1, 3, 6, and 10). In the figure, "a" corresponds to a case of addition of 0.3 mass % glycerin, "b" a case of addition of 1 mass % glycerin, and "c" a case of addition of 3 mass % glycerin.

FIG. 2-4A

Graphs showing non-specific flocculation of latex particles in unsensitized latex reagents in the presence of glycine as an additive, with respect to the number of freezing/thawing operations (0, 1, 3, 6, and 10). In the figure, "a" corresponds to a case of addition of 0.1 mass % glycine, "b" a case of addition of 0.3 mass % glycine, and "c" a case of addition of 1 mass % glycine.

FIG. 2-4B

Additional graphs to the graphs of FIG. 2-4A. In the figure, "d" corresponds to a case of addition of 3 mass % glycine, and "e" corresponds to a case of addition of 10 mass % glycine.

FIG. 2-5A

Graphs showing non-specific flocculation of latex particles in unsensitized latex reagents in the presence of β-alanine as an additive, with respect to the number of freezing/thawing operations (0, 1, 3, 6, and 10). In the figure, "a" corresponds to a case of addition of 0.1 mass % β-alanine, "b" a case of addition of 0.3 mass % β-alanine, and "c" a case of addition of 1 mass % β-alanine.

FIG. 2-5B

Additional graphs to the graphs of FIG. 2-5A. In the figure, "d" corresponds to a case of addition of 3 mass % β-alanine, and "e" corresponds to a case of addition of 10 mass % β-alanine.

FIG. 2-6A

Graphs showing non-specific flocculation of latex particles in unsensitized latex reagents in the presence of 4-aminobutyric acid as an additive, with respect to the number of freezing/thawing operations (0, 1, 3, 6, and 10). In the figure, "a" corresponds to a case of addition of 0.1 mass % 4-aminobutyric acid, "b" a case of addition of 0.3 mass % 4-aminobutyric acid, and "c" a case of addition of 1 mass % 4-aminobutyric acid.

FIG. 2-6B

Additional graphs to the graphs of FIG. 2-6A. In the figure, "d" corresponds to a case of addition of 3 mass % 4-aminobutyric acid, and "e" corresponds to a case of addition of 10 mass % 4-aminobutyric acid.

FIG. 2-7A

Graphs showing non-specific flocculation of latex particles in unsensitized latex reagents in the presence of 5-aminovaleric acid as an additive, with respect to the number of freezing/thawing operations (0, 1, 3, 6, and 10). In the figure, "a" corresponds to a case of addition of 0.1 mass % 5-aminovaleric acid, "b" a case of addition of 0.3 mass % 5-aminovaleric acid, and "c" a case of addition of 1 mass % 5-aminovaleric acid.

FIG. 2-7B

Additional graphs to the graphs of FIG. 2-7A. In the figure, "d" corresponds to a case of addition of 3 mass % 5-aminovaleric acid, and "e" corresponds to a case of addition of 10 mass % 5-aminovaleric acid.

FIG. 2-8A

Graphs showing non-specific flocculation of latex particles in unsensitized latex reagents in the presence of 6-aminohexanoic acid as an additive, with respect to the number of freezing/thawing operations (0, 1, 3, 6, and 10). In the figure, "a" corresponds to a case of addition of 0.1 mass % 6-aminohexanoic acid, "b" a case of addition of 0.3 mass % 6-aminohexanoic acid, and "c" a case of addition of 1 mass % 6-aminohexanoic acid.

FIG. 2-8B

Additional graphs to the graphs of FIG. 2-8A. In the figure, "d" corresponds to a case of addition of 3 mass % 6-aminohexanoic acid, and "e" corresponds to a case of addition of 10 mass % 6-aminohexanoic acid.

FIG. 2-9A

Graphs showing non-specific flocculation of latex particles in unsensitized latex reagents in the presence of 7-aminoheptanoic acid as an additive, with respect to the number of freezing/thawing operations (0, 1, 3, 6, and 10). In the figure, "a" corresponds to a case of addition of 0.1 mass % 7-aminoheptanoic acid, "b" a case of addition of 0.3 mass % 7-aminoheptanoic acid, and "c" a case of addition of 1 mass % 7-aminoheptanoic acid.

FIG. 2-9B

Additional graphs to the graphs of FIG. 2-9A. In the figure, "d" corresponds to a case of addition of 3 mass % 7-aminoheptanoic acid, and "e" corresponds to a case of addition of 10 mass % 7-aminoheptanoic acid.

FIG. 3-1

Graph showing non-specific flocculation of latex particles in sensitized latex reagents in the absence of an additive, with respect to the number of freezing/thawing operations (0, 1, 3, 6, and 10).

FIG. 3-2A

Graphs showing non-specific flocculation of latex particles in sensitized latex reagents in the presence of glycine as an additive, with respect to the number of freezing/thawing operations (0, 1, 3, 6, and 10). In the figure, "a" corresponds to a case of addition of 0.1 mass % glycine, and "b" corresponds to a case of addition of 0.3 mass % glycine.

FIG. 3-2B

Additional graphs to the graphs of FIG. 3-2A. In the figure, "c" corresponds to a case of addition of 3 mass % glycine, and "d" corresponds to a case of addition of 10 mass % glycine.

FIG. 3-3A

Graphs showing non-specific flocculation of latex particles in sensitized latex reagents in the presence of β-alanine as an additive, with respect to the number of freezing/thawing operations (0, 1, 3, 6, and 10). In the figure, "a" corresponds to a case of addition of 0.1 mass % β-alanine, and "b" corresponds to a case of addition of 0.3 mass % β-alanine.

FIG. 3-3B

Additional graphs to the graphs of FIG. 3-3A. In the figure, "c" corresponds to a case of addition of 3 mass % β-alanine, and "d" corresponds to a case of addition of 10 mass % β-alanine.

FIG. 3-4A

Graphs showing non-specific flocculation of latex particles in sensitized latex reagents in the presence of 4-aminobutyric acid as an additive, with respect to the number of freezing/thawing operations (0, 1, 3, 6, and 10). In the figure, "a" corresponds to a case of addition of 0.1 mass % 4-aminobutyric acid, and "b" corresponds to a case of addition of 0.3 mass % 4-aminobutyric acid.

FIG. 3-4B

Additional graphs to the graphs of FIG. 3-4A. In the figure, "c" corresponds to a case of addition of 3 mass % 4-aminobutyric acid, and "d" corresponds to a case of addition of 10 mass % 4-aminobutyric acid.

FIG. 3-5A

Graphs showing non-specific flocculation of latex particles in sensitized latex reagents in the presence of 5-aminovaleric acid as an additive, with respect to the number of freezing/thawing operations (0, 1, 3, 6, and 10). In the figure, "a" corresponds to a case of addition of 0.1 mass % 5-aminovaleric acid, and "b" corresponds to a case of addition of 0.3 mass % 5-aminovaleric acid.

FIG. 3-5B

Additional graphs to the graphs of FIG. 3-5A. In the figure, "c" corresponds to a case of addition of 3 mass % 5-aminovaleric acid, and "d" corresponds to a case of addition of 10 mass % 5-aminovaleric acid.

FIG. 3-6A

Graphs showing non-specific flocculation of latex particles in sensitized latex reagents in the presence of 6-aminohexanoic acid as an additive, with respect to the number of freezing/thawing operations (0, 1, 3, 6, and 10). In the figure, "a" corresponds to a case of addition of 0.1 mass % 6-aminohexanoic acid, "b" a case of addition of 0.3 mass % 6-aminohexanoic acid, and "c" a case of addition of 1 mass % 6-aminohexanoic acid.

FIG. 3-6B

Additional graphs to the graphs of FIG. 3-6A. In the figure, "d" corresponds to a case of addition of 3 mass % 6-aminohexanoic acid, and "e" corresponds to a case of addition of 10 mass % 6-aminohexanoic acid.

FIG. 3-7A

Graphs showing non-specific flocculation of latex particles in sensitized latex reagents in the presence of 7-aminoheptanoic acid as an additive, with respect to the number of freezing/thawing operations (0, 1, 3, 6, and 10). In the figure, "a" corresponds to a case of addition of 0.1 mass % 7-aminoheptanoic acid, and "b" corresponds to a case of addition of 0.3 mass % 7-aminoheptanoic acid.

FIG. 3-7B

Additional graphs to the graphs of FIG. 3-7A. In the figure, "c" corresponds to a case of addition of 3 mass % 7-aminoheptanoic acid, and "d" corresponds to a case of addition of 10 mass % 7-aminoheptanoic acid.

FIG. 4A

Graphs showing non-specific flocculation of colloidal gold particles in sensitized colloidal gold reagents in the presence of 6-aminohexanoic acid as an additive, with respect to the number of freezing/thawing operations (0, 1, 3, 6, and 10). In the figure, "a" corresponds to a case of addition of 0 mass % 6-aminohexanoic acid, and "b" corresponds to a case of addition of 0.3 mass % 6-aminohexanoic acid.

FIG. 4B

Additional graphs to the graphs of FIG. 4A. In the figure, "c" corresponds to a case of addition of 1 mass % 6-aminohexanoic acid, and "d" corresponds to a case of addition of 3 mass % 6-aminohexanoic acid.

MODES FOR CARRYING OUT THE INVENTION

[Immunoassay Reagent]

The immunoassay reagent of the present invention contains, as a degradation preventing component, ω-aminocarboxylic acid (1), wherein the number of carbon atoms n is an integer of 2 to 6, more specifically 2, 3, 4, 5, or 6.

Whether the insoluble carrier particles are unsensitized or sensitized, n is preferably an integer of 2 to 5, with an integer of 5 being most preferred in both cases (i.e., unsensitized and sensitized). That is, 6-aminohexanoic acid is most preferred.

In the case where insoluble carrier particles is unsensitized, the concentration of ω-aminocarboxylic acid (1) in the reagent is preferably 0.1 to 10 mass %, more preferably 0.3 to 3 mass %. In the case where insoluble carrier particles are sensitized, the concentration is preferably 3 to 10 mass % when n is an integer of 2 to 5; and the concentration is preferably 0.1 to 0.3 mass % when n is 6.

So long as the same variation in measurements after freezing/thawing can be ensured, the concentration of co-aminocarboxylic acid (1) is preferably lower. This is because the measurement sensitivity tends to be lowered at higher concentration.

Examples of the aqueous solvent for the immunoassay reagent of the present invention include water and a buffer, as mentioned above. No particular limitation is imposed on the buffer, and examples include a glycine buffer, a borate buffer, and Good's buffer. Also in the present invention, appropriate additives such as BSA, gum arabic, a surfactant, choline, a chelating agent, and an antiseptic agent may be used in such a quality and an amount that the effects of the invention are not virtually impaired. The pH of the aqueous solvent is preferably controlled so as not to impair a target antigen-antibody reaction. More specifically, the pH is preferably about 4 to about 9, particularly preferably about 6 to about 9.

No particular limitation is imposed on the mean particle size of the insoluble carrier particles, so long as the size allows the particles to be used in the immunoassay reagent. In the case of latex particles, the mean particle size may be widely selected from a range of about 0.01 to about 1 μm, whereas in the case of colloidal gold particles, the mean particle size may be selected from a range of 0.005 to 0.1 μm.

In the case where the insoluble carrier particles such as latex particles and colloidal gold particles are unsensitized, the following technique may be employed, as mentioned above. In the technique, the target protein in a specimen is caused to be directly adsorbed onto the carrier particles, and a corresponding antibody is caused to react with the target protein. No particular limitation is imposed on the target protein, and examples include hemoglobin A1c.

In the case where the insoluble carrier particles are sensitized, the mode of attaching a sensitizing antigen or antibody is not limited. In the case of latex particles, either physical adsorption or chemical bonding may be employed. The sensitizing antigen may be freely selected in accordance with the target antibody in the body. No particular limitation is imposed on the sensitizing antigen, and examples include a syphilitic antigen and streptolysin O. The sensitizing antibody may be freely selected in accordance with the target antigen. Moreover, the sensitizing antibody may be a monoclonal antibody or a polyclonal antibody, and the globulin (as a molecule) may be selected from any of the classes of IgG, IgM, IgA, IgD, and IgE. No particular limitation is imposed on the subclass, and the entirety or a part of the globulin molecule may be employed.

[Degradation Prevention Method]

In the degradation prevention method of the present invention, co-presence of the aforementioned ω-aminocarboxylic acid (1) in the immunoassay reagent containing a sensitized or unsensitized insoluble carrier particles can be realized in the following manner. Specifically, ω-aminocarboxylic acid (1) is added to the reagent in any step of production of the immunoassay reagent so as to attain a specific concentration. Addition of the ω-aminocarboxylic acid (1) may be performed before or after addition of the insoluble carrier particles.

The immunoassay reagent subjected to the degradation prevention method of the present invention does not cause non-specific flocculation of insoluble carrier particles during a freezing/thawing process. As a result, degradation of the immunoassay reagent can be prevented.

The immunoassay reagent of the present invention is the thus-produced immunoassay reagent.

EXAMPLES

Specific examples of the present invention will next be described. Unless otherwise specified, the unit "%" refers to the unit "mass %" with respect to the incorporation object. Also, unless otherwise specified, the description of the number "n," for example "n=5," refers to co-aminocarboxylic acid (1) (n=5). As described above, the ω-aminocarboxylic acid (1) is represented by the following formula (1):

[F2]

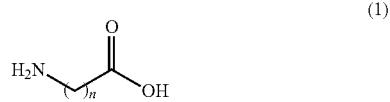
(1)

[Wherein n is an Integer of 2 to 6].

[Example 1] Studies on Unsensitized Latex

<Preparation of First Reagent (Unsensitized Latex Dispersion)>

To a buffer containing 10-mmol/mL HEPES, there was added any of (1) no substance (as a comparative example), (2) trehalose dihydrate (product of Hayashibara, as comparative example), (3) glycerin (product of Wako Pure Chemical Industries, Ltd., as a comparative example), (4) glycine (product of Wako Pure Chemical Industries, Ltd., as a comparative example), (5) β-alanine (n=2, product of Tokyo Chemical Industry, Co., Ltd.), (6) 4-aminobutyric acid (n=3, product of Tokyo Chemical Industry, Co., Ltd.), (7) 5-aminovaleric acid (n=4, product of Tokyo Chemical Industry, Co., Ltd.), (8) 6-aminohexanoic acid (n=5, product of Wako Pure Chemical Industries, Ltd.), and (9) 7-aminoheptanoic acid (n=6, product of Tokyo Chemical Industry, Co., Ltd.), and each substance was dissolved in the buffer (substance concentration: 0.3%, 1%, and 3% in cases (2) and (3), or substance concentration: 0.1%, 0.3%, 1%, 3%, and 10% in cases of (4), (5), (6), (7), (8), and (9)). To each of the thus-created systems, unsensitized polystyrene latex particles (mean particle size: 0.12 μm: product of Fujikura Kasei, Co., Ltd.) were added so as to adjust the particle content to 0.1%, and then the pH was adjusted to 7.9 by use of aqueous sodium hydroxide. Finally, 37 samples of unsensitized latex dispersion were prepared.

<Observation of Change in Particle Size in First Reagent after Freezing/Thawing of the Reagent>

Each of the above-prepared first reagents (latex dispersions) was repeatedly subjected to freezing/thawing operations 0 to 10 times (specifically, 0, 1, 3, 6, and 10 times). After each of the repeated freezing/thawing operations, the mean particle size of the latex particles was measured, while the particles remained in the sample. In each freezing/thawing operation, the reagent was frozen by means of a freezer at −30° C. for 3 hours, and thereafter, the frozen product was allowed to stand at room temperature (about 25° C.), to thereby complete thawing to liquid. This freezing/thawing procedure is referred to as "one time" freezing/thawing operation. The mean particle size in the sample was measured by means of Fiber Optics Particle Analyzer FPAR-1000 (product of Otsuka Electronics Co., Ltd.). FIG. 1 shows the results.

As is clear in FIG. 1, the latex particle size of the samples to which a predetermined amount of ω-aminocarboxylic acid (1) had been added was virtually unchanged before and after a freezing/thawing operation.

<Preparation of Second Reagent (Antibody Dilute Solution)>

To a buffer containing 10-mmol/mL HEPES, sodium chloride was added to a concentration of 20 g/L. Then, 0.2% Tween-20 was added thereto, and the pH of the mixture was adjusted to 7.0. To an appropriate volume of the thus-prepared buffer solution, an anti-human HbA1c mouse monoclonal antibody (product of Fujikura Kasei, Co., Ltd.), an anti-mouse IgG goat polyclonal antibody (Product of Wako Chemical Industries, Ltd.), and hydroxypropyl cellulose were added to adjust their concentrations to 0.05 mg/mL, 0.2 mg/mL, and 1%, respectively, whereby an antibody dilute solution was prepared.

<Observation of Variation in Calibration Curves Due to Freezing/Thawing by Use of the First and Second Reagents>

In the same manner as employed above, the first reagents were repeatedly subjected to freezing/thawing operations 0 to 10 times (specifically, 0, 1, 3, 6, and 10 times). A calibration curve (change in absorbance vs. HbA1c concentration) was drawn with respect to each sample at any time of repeated freezing/thawing operations. The samples for drawing calibration curves were purified human HbA1c samples having an HbA1c concentration of 0%, 4.2%, 8.5%, 12.0%, and 16.4%. Each sample (6 μL) was mixed with a first reagent (150 μL), and the mixture was allowed to react at 37° C. for 5 minutes. Subsequently, a second reagent (50 μL) was added to the reaction mixture, and a change in absorbance within a time range of 5 minutes was determined by means of Hitachi Auto Analyzer 7180 through the 2-point end technique (main wavelength: 660 nm, sub-wavelength: 800 nm). FIG. 2 (FIGS. 2-1, 2-2, 2-3, 2-4A, 2-4B, 2-5A, 2-5B, 2-6A, 2-6B, 2-7A, 2-7B, 2-8A, 2-8B, 2-9A, and 2-9B) show the results.

From the results shown in FIG. 2, it became clear that the latex particles in a system to which a predetermined amount of ω-aminocarboxylic acid (1) had been added were less likely to cause non-specific flocculation even by a freezing/thawing operation or repeated freezing/thawing operations. The cases where n is 2 to 5 were preferred, with the case where n is 5 being most preferred.

[Example 2] Studies on Sensitized Latex

<Preparation of Third Reagent (Sample Dilute Solution)>

To a buffer containing 50-mM glycine, sodium chloride was added to a concentration of 0.15 mol/mL. The pH of the mixture was adjusted to 9.0 by use of aqueous sodium hydroxide, to thereby prepare a sample dilute solution.

<Preparation of Fourth Reagent (Antibody Sensitized Latex Dispersion)>

An anti-human Lp(a) goat polyclonal antibody (product of Torina Bio Reactives) (100 mg) was added to a 50-mM borate buffer (20 mL), and 10% latex dispersion (12.5 mL) of unsensitized polystyrene latex particles (mean particle size: 0.12 μm: product of Fujikura Kasei, Co., Ltd.) was added thereto. The resultant mixture was ultra-sonicated by means of an ultra-sonicator VCX750 (product of SONIC & MATERIALS INC.) for 1 minute under cooling with ice. Subsequently, the product was stirred at room temperature for 30 minutes, and 5% aqueous BSA (7 mL) was added, followed by stirring at 50° C. for 30 minutes. Then, the mixture was centrifuged at 20,000 G for 20 minutes, and the supernatant was removed to obtain the sensitized polystyrene latex particles. In 10-mmol/mL HEPES, any of (1) no substance (as a comparative example), (2) glycine (product of Wako Pure Chemical Industries, Ltd., as a comparative example), (3) β-alanine (n=2, product of Tokyo Chemical Industry, Co., Ltd.), (4) 4-aminobutyric acid (n=3, product of Tokyo Chemical Industry, Co., Ltd.), (5) 5-aminovaleric acid (n=4, product of Tokyo Chemical Industry, Co., Ltd.), (6) 6-aminohexanoic acid (n=5, product of Wako Pure Chemical Industries, Ltd.), and (7) 7-aminoheptanoic acid (n=6, product of Tokyo Chemical Industry, Co., Ltd.) was dissolved (substance concentration: 0.1%, 0.3%, 3%, and 10% (in the case (6), substance concentration: 0.1%, 0.3%, 1%, 3%, and 10%)). To each of the thus-created systems, the aforementioned sensitized polystyrene latex particles (mean particle size: 0.12 μm: product of Fujikura Kasei, Co., Ltd.) were added so as to adjust the particle content to 0.3%. Finally, 26 samples of antibody-sensitized latex dispersion were prepared.

<Observation of Variation in Calibration Curves Due to Freezing/Thawing by Use of the Third and Fourth Reagents>

In the same manner as employed above, the fourth reagents were repeatedly subjected to freezing/thawing operations 0 to 10 times. A calibration curve (change in absorbance vs. Lp(a) concentration) was drawn with respect to each sample at any time of repeated freezing/thawing operations. The samples for drawing calibration curves were purified Lp(a) samples having an Lp(a) concentration of 0 mg/dL, 15 mg/dL, 30 mg/dL, 60 mg/dL, and 100 mg/dL. Each sample (2.1 μL) was mixed with a third reagent (210 μL), and the mixture was allowed to react at 37° C. for 5 minutes. Subsequently, a fourth reagent (70 μL) was added to the reaction mixture, and a change in absorbance within a time range of 5 minutes was determined by means of Hitachi Auto Analyzer 7180 through the 2-point end technique (main wavelength: 600 nm). FIG. 3 (FIGS. 3-1, 3-2A, 3-2B, 3-3A, 3-3B, 3-4A, 3-4B, 3-5A, 3-5B, 3-6A, 3-6B, 3-7A, 3-7B, 3-8A, and 3-8B) show the results.

From the results shown in FIG. 3, it was revealed that non-specific flocculation of the sensitized latex particles due to a freezing/thawing operation or repeated freezing/thawing operations can be prevented by each of the ω-aminocarboxylic acid (1) in which n is an integer of 2 to 6. The effect of preventing non-specific flocculation was preferably attained at the concentration of 3 to 10% when n was an integer of 2 to 5. In the case where n is 6, the concentration of 0.1 to 0.3% was found to be preferred. In particular, 6-aminohexanoic acid (i.e., m-aminocarboxylic acid (1), wherein n is 5) was found to most prevent non-specific flocculation of sensitized latex particles due to freezing/thawing, at a concentration of 3% from the viewpoint of assay sensitivity and prevention of non-specific flocculation.

[Example 3] Studies on Sensitized Gold Colloid

<Preparation of Fifth Reagent (Antibody Sensitized Gold Colloid Dispersion)>

A gold colloid dispersion (product of Roche Diagnostic K. K.) (350 mL) was mixed with 500-mM HEPES (pH: 7) (7 mL), and an anti-human CRP goat polyclonal antibody (product of ADVY) (2.1 mg) was added thereto, followed by stirring at room temperature for 1 hour. Subsequently, 0.1% aqueous BSA (38.5 mL) was added thereto, and the resultant mixture was stirred at room temperature for 30 minutes. Thereafter, the resultant mixture was centrifuged at 20,000 G for 20 minutes, and the supernatant was removed, to which a buffer (42 mL) prepared by adding 6-aminohexanoic acid (0.3%, 1%, or 3%) to 10-mmol/mL HEPES was added to thereby prepare an antibody sensitized gold colloid dispersion.

<Observation of Variation in Calibration Curves Due to Freezing/Thawing by Use of the Third and Fifth Reagents>

In the same manner as employed above, the fourth reagents were repeatedly subjected to freezing/thawing operations 0 to 10 times. A calibration curve (change in absorbance vs. CRP concentration) was drawn with respect to each sample at any time of repeated freezing/thawing operations. The samples for drawing calibration curves were purified CRP samples having a CRP concentration of 0 mg/dL, 0.02 mg/dL, 0.05 mg/dL, 0.09 mg/dL, 0.19 mg/dL, 0.38 mg/dL, and 0.75 mg/dL. Each sample (2.1 μL) was mixed with a third reagent (140 μL), and the mixture was allowed to react at 37° C. for 5 minutes. Subsequently, a fifth reagent (140 μL) was added to the reaction mixture, and a change in absorbance within a time range of 5 minutes was determined by means of Hitachi Auto Analyzer 7180 through the 2-point end technique (main wavelength: 600 nm).

FIG. 4 (FIGS. 4A and 4B) show the results.

As is clear from FIG. 4, 6-aminohexanoic acid (i.e., ω-aminocarboxylic acid (1), wherein n is 5) was found to suppress non-specific flocculation of the sensitized gold colloid which would otherwise be caused by freezing/thawing.

INDUSTRIAL APPLICABILITY

In the immunoassay reagent of the present invention and the immunoassay reagents subjected to the degradation prevention method of the present invention, non-specific flocculation of insoluble carrier particles such as latex particles and colloidal gold particles can be prevented, even under severe storage conditions, for example, where a liquid-form reagent is frozen, or even under unstable temperature control conditions during transport thereof. Thus, the present invention enables storage of immunoassay reagents without degrading their detection performance, and greatly contributes to convenience of storage and transport of immunoassay reagents. Furthermore, the present invention significantly differs from similar conventional techniques in that the present invention is also applicable to sensitized insoluble carrier particles. In other words, the present invention enables stable storage of an immunoassay reagent employing sensitized insoluble carrier particles in a detection system. The present invention can also facilitate storage and transport of an immunoassay reagent employing sensitized and unsensitized insoluble carrier particles that coexist in a detection system, which is used, for example, in the case where a plurality of diagnostic terms are analyzed by means of a small special analyzer.

The entirety of the disclosures of Japanese Patent Application Nos. 2017-149290 (Filing date: Aug. 1, 2017) and 2017-208678 (Filing date: Oct. 27, 2017) are incorporated herein by reference. All the documents, patent applications, and technical standards disclosed herein are incorporated herein by reference to the same extent as if each document, patent application, or technical standard was specifically and individually described to be incorporated herein by reference.

The invention claimed is:

1. An immunoassay reagent comprising, in a solvent, sensitized insoluble carrier particles and an ω-aminocarboxylic acid represented by the following formula (1):

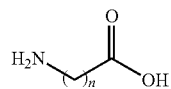

(1)

wherein n is 6,
wherein the concentration of the ω-aminocarboxylic acid is 0.1 to 0.3 mass % of the reagent.

2. The immunoassay reagent according to claim 1, which is an immunoassay reagent by an agglutination method.

3. The immunoassay reagent according to claim 1, wherein the insoluble carrier particles are latex particles or colloidal gold particles.

4. A method for preventing degradation of an immunoassay reagent, the method comprising causing an ω-aminocarboxylic acid represented by the following formula (1):

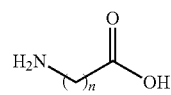

(1)

wherein n is 6,
to be co-present in an immunoassay reagent comprising sensitized insoluble carrier particles, to thereby prevent non-specific flocculation of the insoluble carrier particles,
wherein the concentration of the ω-aminocarboxylic acid is 0.1 to 0.3 mass % of the reagent.

5. The degradation prevention method according to claim 4, wherein the immunoassay reagent is an immunoassay reagent by an agglutination method.

6. The degradation prevention method according to claim 4, wherein the insoluble carrier particles are latex particles or colloidal gold particles.

* * * * *